(12) United States Patent
Yamasaki et al.

(10) Patent No.: US 9,720,137 B2
(45) Date of Patent: Aug. 1, 2017

(54) EYEWEAR MATERIAL, EYEWEAR FRAME, AND EYEWEAR

(71) Applicant: MITSUI CHEMICALS, INC., Tokyo (JP)

(72) Inventors: Satoshi Yamasaki, Chiba (JP); Goro Kuwamura, Chiba (JP); Daisuke Nishiguchi, Sakai (JP); Daisuke Hasegawa, Yokohama (JP); Toshihiko Nakagawa, Ichihara (JP); Hirokazu Morita, Chiba (JP); Hidetaka Tsukada, Omuta (JP); Kenichi Goto, Chiba (JP); Shinsuke Ito, Omuta (JP); Naoyuki Kakinuma, Omuta (JP); Tetsuya Hamada, Ichihara (JP); Shinji Kiyono, Kimitsu (JP); Takeshi Fukuda, Kurume (JP); Kazuhiro Kosumi, Omuta (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 15/024,052

(22) PCT Filed: Sep. 25, 2014

(86) PCT No.: PCT/JP2014/075512
§ 371 (c)(1),
(2) Date: Mar. 23, 2016

(87) PCT Pub. No.: WO2015/046370
PCT Pub. Date: Apr. 2, 2015

(65) Prior Publication Data
US 2016/0238857 A1    Aug. 18, 2016

(30) Foreign Application Priority Data

Sep. 26, 2013 (JP) ................. 2013-200500
Jun. 19, 2014 (JP) ................. 2014-126296

(51) Int. Cl.
*G02C 7/02* (2006.01)
*G02B 1/04* (2006.01)
(Continued)

(52) U.S. Cl.
CPC .............. *G02B 1/041* (2013.01); *A47D 1/00* (2013.01); *C07C 263/20* (2013.01); *C07C 265/04* (2013.01); *C07C 265/14* (2013.01); *C07D 295/067* (2013.01); *C07D 295/08* (2013.01); *C07D 295/10* (2013.01); *C07D 295/104* (2013.01); *C07D 295/108* (2013.01); *C07D 295/16* (2013.01); *C07D 295/185* (2013.01); *C08G 18/10* (2013.01); *C08G 18/283* (2013.01); *C08G 18/3206* (2013.01); *C08G 18/3275* (2013.01); *C08G 18/3855* (2013.01); *C08G 18/3878* (2013.01); *C08G 18/4018* (2013.01); *C08G 18/4063* (2013.01); *C08G 18/4202* (2013.01); *C08G 18/4277* (2013.01); *C08G 18/44* (2013.01); *C08G 18/4808* (2013.01); *C08G 18/4825* (2013.01); *C08G 18/4854* (2013.01); *C08G 18/6229* (2013.01); *C08G 18/6677* (2013.01); *C08G 18/722* (2013.01); *C08G 18/73* (2013.01); *C08G 18/757* (2013.01); *C08G 18/758* (2013.01); *C08G 18/7642* (2013.01); *C08G 18/7818* (2013.01); *C08G 18/7831* (2013.01); *C08G 18/7837* (2013.01); *C08G 18/7843* (2013.01); *C08G 18/792* (2013.01); *C08J 5/18* (2013.01); *C08K 5/3412* (2013.01); *C08L 75/08* (2013.01);
(Continued)

(58) Field of Classification Search
CPC .... A47D 1/00; C08G 18/3878; C08G 18/722; C08G 18/6677; C08G 18/4063; C08G 18/6229; C08G 18/4808; C08G 18/7642; C08G 18/4825; C08G 18/3206; C08G 18/10; C08G 18/7843; C08G 18/7831; C08G 18/7837; C08G 18/7818; C09D 175/04; C08L 75/08; D04H 3/009; D01F 6/70; G02B 1/041; G02B 1/04; G02C 5/008; G02C 5/00; Y10T 442/60; Y10T 428/249921
USPC ................... 351/41, 66, 87, 159.01
See application file for complete search history.

(56) References Cited

U.S. PATENT DOCUMENTS 4,120,848 A    10/1978    Ueda
6,204,300 B1    3/2001    Kumaki
(Continued)

FOREIGN PATENT DOCUMENTS

CN    1450365    10/2003
JP    354218    3/1991
(Continued)

OTHER PUBLICATIONS

International Search Report dated Nov. 18, 2014 filed in PCT/JP2014/075512.
(Continued)

*Primary Examiner* — Tuyen Tra
(74) *Attorney, Agent, or Firm* — Rankin, Hill & Clark LLP

(57) ABSTRACT

The eyewear material is an eyewear material containing thermoplastic polyurethane. The eyewear material has a tan δ peak at both less than 0° C. and 0° C. or more and 70° C. or less observed in dynamic viscoelasticity measurement in tensile mode under the measurement conditions of a temperature increase speed of 5° C./min and a measurement frequency of 10 Hz.

9 Claims, No Drawings

(51) Int. Cl.
| | |
|---|---|
| *C08J 5/18* | (2006.01) |
| *D04H 3/009* | (2012.01) |
| *G02C 5/00* | (2006.01) |
| *C08G 18/79* | (2006.01) |
| *C08K 5/3412* | (2006.01) |
| *C07C 265/04* | (2006.01) |
| *C07C 265/14* | (2006.01) |
| *C07D 295/08* | (2006.01) |
| *C07D 295/067* | (2006.01) |
| *C07D 295/10* | (2006.01) |
| *C07D 295/104* | (2006.01) |
| *C07D 295/108* | (2006.01) |
| *C07D 295/16* | (2006.01) |
| *C07D 295/185* | (2006.01) |
| *C08G 18/78* | (2006.01) |
| *C08G 18/48* | (2006.01) |
| *C08G 18/73* | (2006.01) |
| *C08G 18/75* | (2006.01) |
| *C08G 18/28* | (2006.01) |
| *C08G 18/32* | (2006.01) |
| *C08G 18/38* | (2006.01) |
| *C08G 18/40* | (2006.01) |
| *C08G 18/42* | (2006.01) |
| *C08G 18/44* | (2006.01) |
| *C07C 263/20* | (2006.01) |
| *C08G 18/10* | (2006.01) |
| *C08L 75/08* | (2006.01) |
| *C09D 175/04* | (2006.01) |
| *A47D 1/00* | (2006.01) |
| *C08G 18/62* | (2006.01) |
| *C08G 18/66* | (2006.01) |
| *C08G 18/72* | (2006.01) |
| *C08G 18/76* | (2006.01) |
| *C08G 101/00* | (2006.01) |
| *D01F 6/70* | (2006.01) |

(52) U.S. Cl.
 CPC ........... *C09D 175/04* (2013.01); *D04H 3/009* (2013.01); *G02B 1/04* (2013.01); *G02C 5/00* (2013.01); *G02C 5/008* (2013.01); *C08G 2101/00* (2013.01); *C08G 2170/20* (2013.01); *C08G 2190/00* (2013.01); *C08J 2375/04* (2013.01); *D01F 6/70* (2013.01); *Y10T 428/249921* (2015.04); *Y10T 442/60* (2015.04)

(56) References Cited

U.S. PATENT DOCUMENTS

| | | | |
|---|---|---|---|
| 8,188,171 B2 * | 5/2012 | Bernard | ............... C08G 18/544 427/385.5 |
| 2003/0195323 A1 | 10/2003 | Tamura et al. | |
| 2004/0087754 A1 | 5/2004 | Foley | |
| 2009/0005467 A1 | 1/2009 | Moriya | |
| 2010/0216905 A1 | 8/2010 | Kuwamura | |
| 2010/0249264 A1 | 9/2010 | Hu et al. | |
| 2013/0035466 A1 | 2/2013 | Vanlandschoot | |
| 2013/0338330 A1 | 12/2013 | Sato | |

FOREIGN PATENT DOCUMENTS

| | | |
|---|---|---|
| JP | 5289030 A2 | 11/1993 |
| JP | 11286566 A2 | 10/1999 |
| JP | 2010190919 A2 | 9/2010 |
| JP | 2010280884 A2 | 12/2010 |
| JP | 2012097279 A2 | 5/2012 |
| JP | 2013040310 A2 | 2/2013 |
| JP | 2013521367 T2 | 6/2013 |
| JP | 2013213222 A2 | 10/2013 |
| WO | 2007077792 A1 | 7/2007 |
| WO | 2008144614 A1 | 11/2008 |
| WO | 2009051114 A1 | 4/2009 |
| WO | 2012121291 A1 | 9/2012 |

OTHER PUBLICATIONS

International Preliminary Report on Patentability dated Nov. 18, 2014 filed in PCT/JP2014/075512, total 15 pages.
Extended European Search Report dated Apr. 4, 2017 issued in the corresponding European paten application No. 14847268.1.

* cited by examiner

EYEWEAR MATERIAL, EYEWEAR FRAME, AND EYEWEAR

TECHNICAL FIELD

The present invention relates to an eyewear material, an eyewear frame, and an eyewear. In particular, the present invention relates to an eyewear material, an eyewear frame produced by using the eyewear material, and an eyewear including the eyewear frame.

BACKGROUND ART

Conventionally, eyewear such as corrective glasses, protection glasses, sunglasses, and goggles include a lens and a frame. In such eyewear, frames are formed from, for example, metal materials such as pure titanium, nickel-titanium alloys, aluminum, magnesium, and gold; synthetic resin materials such as celluloid, acetate, and polyamide resin; and natural materials such as tortoiseshell.

Meanwhile, there are demands for improvements in mechanical properties (mechanical strength, etc.) and processability for eyewear. Thus, use of polyurethane elastomers having excellent mechanical properties and processability as an eyewear material have been examined.

To be more specific, for example, Patent Document 1 has proposed use of hard thermoplastic polyurethane produced by reacting diisocyanate including bis(isocyanatomethyl) cyclohexane and diol including cyclohexanedimethanol as an eyewear frame.

Furthermore, Patent Document 2 has proposed using, for example, when producing a spectacle frame using thermoplastic polyurethane resin, a thermoplastic polyurethane resin having a difference between the crystallization peak temperature and the glass transition temperature observed in DSC (derivative scanning calorimeter) analysis of 27° C. or more, and having a Shore D hardness of 74 or more.

Citation List

Patent Document

Patent Document 1:
Japanese Unexamined Patent Publication No. 2013-213222
Patent Document 2:
Japanese Unexamined Patent Publication No. H3-54318

SUMMARY OF THE INVENTION

Problem to be Solved by the Invention

Meanwhile, eyewear are directly worn on the face, and therefore contact and fit are important.

An object of the present invention is to provide an eyewear material having excellent mechanical strength and processability and also excellent comfortability such as fit and contact, an eyewear frame produced by using the eyewear material, and an eyewear including the eyewear frame.

Means for Solving the Problem

An eyewear material of the present invention is an eyewear material containing thermoplastic polyurethane, and the eyewear material has a tan δ peak at both less than 0° C. and 0° C. or more and 70° C. or less observed in dynamic viscoelasticity measurement in tensile mode under the measurement conditions of a temperature increase speed of 5° C./min and a measurement frequency of 10 Hz.

In the eyewear material of the present invention, it is preferable that the thermoplastic polyurethane has a hard segment concentration of 25 mass % or more and 70 mass % or less.

In the eyewear material of the present invention, it is preferable that the thermoplastic polyurethane is produced by reaction of a polyisocyanate component containing bis(isocyanatomethyl) cyclohexane with an active hydrogen group-containing component.

It is preferable that the eyewear material of the present invention further contains 0.01 parts by mass or more and 1 part by mass or less of acryl-modified organopolysiloxane relative to 100 parts by mass of the thermoplastic polyurethane.

An eyewear frame of the present invention is formed from the above-described eyewear material.

It is preferable that the eyewear frame of the present invention is coated with a polyurethane coating agent containing aliphatic polyisocyanate.

In the eyewear frame of the present invention, it is preferable that the aliphatic polyisocyanate contains pentamethylenediisocyanate and/or its derivative.

An eyewear of the present invention includes the above-described eyewear frame and an optical lens attached to the eyewear frame.

In the eyewear of the present invention, it is preferable that the optical lens is formed from a biomass material.

Effects of the Invention

The eyewear material, the eyewear frame, and the eyewear of the present invention contain thermoplastic polyurethane, and therefore are excellent in processability and mechanical strength. Furthermore, the eyewear material, the eyewear frame, and the eyewear of the present invention have a tan δ peak based on dynamic viscoelasticity measurement of less than 0° C., and therefore excellent contact can be achieved, and moreover, have a tan δ peak based on dynamic viscoelasticity measurement of 0° C. or more and 70° C. or less, and therefore excellent fit can be achieved.

DESCRIPTION OF EMBODIMENTS

The eyewear material of the present invention contains, as a main component, thermoplastic polyurethane.

The eyewear material contains, for example, 80 mass % or more, preferably 90 mass % or more, and more preferably 95 mass % or more of the thermoplastic polyurethane relative to a total amount of the eyewear material.

The thermoplastic polyurethane is produced by reaction of a polyisocyanate component with an active hydrogen group-containing component.

Examples of the polyisocyanate component include polyisocyanate monomers and polyisocyanate derivatives.

Examples of the polyisocyanate monomer include aromatic polyisocyanates, aralkyl polyisocyanates, and aliphatic polyisocyanates.

Examples of the aromatic polyisocyanate include aromatic diisocyanates such as tolylene diisocyanate (2,4- or 2,6-tolylene diisocyanate or a mixture thereof)(TDI), phenylenediisocyanate (m-, p-phenylenediisocyanate or a mixture thereof), 4,4'-diphenyl diisocyanate, 1,5-naphthalene diisocyanate (NDI), diphenylmethanediisocyanate (4,4'-, 2,4'- or 2,2'-diphenylmethanediisocyanate or a mixture thereof)(MDI), 4,4'-toluidine diisocyanate (TODI), and 4,4'-diphenylether diisocyanate.

Examples of the aralkyl polyisocyanate include aralkyldiisocyanates such as xylylene diisocyanate (1,3- or 1,4-xylylene diisocyanate or a mixture thereof)(XDI), tetramethylxylylene diisocyanate (1,3- or 1,4-tetramethylxylylene diisocyanate or a mixture thereof)(TMXDI), and ω,ω'-diisocyanate-1,4-diethylbenzene.

Examples of the aliphatic polyisocyanate include aliphatic diisocyanates such as trimethylene diisocyanate, 1,2-propylene diisocyanate, butylene diisocyanate (tetramethylenediisocyanate, 1,2-butylenediisocyanate, 2,3-butylenediisocyanate, and 1,3-butylenediisocyanate), 1,5-pentamethylenediisocyanate (PDI), 1,6-hexamethylenediisocyanate (HDI), 2,4,4- or 2,2,4-trimethylhexamethylenediisocyanate, and 2,6-diisocyanatemethylcuprate.

The aliphatic polyisocyanate include an alicyclic polyisocyanate.

Examples of the alicyclic polyisocyanate include alicyclic diisocyanates such as 1,3-cyclopentanediisocyanate, 1,3-cyclopentene diisocyanate, cyclohexanediisocyanate (1,4-cyclohexanediisocyanate, 1,3-cyclohexanediisocyanate), 3-isocyanatomethyl-3,5,5-trimethylcyclohexyl isocyanate (isophoron diisocyanate)(IPDI), methylenebis(cyclohexyl isocyanate)(4,4'-, 2,4'- or 2,2'-methylenebis(cyclohexyl isocyanate, trans-trans isomer thereof, trans-cis isomer thereof, cis-cis isomer thereof, or a mixture thereof)) ($H_{12}$MDI), methylcyclohexanediisocyanate (methyl-2,4-cyclohexanediisocyanate, methyl-2,6-cyclohexanediisocyanate), 2,5 (6)-diisocyanatomethyl[2,2,1]heptane (various isomers or a mixture thereof), and bis(isocyanatomethyl) cyclohexane (1,2-, 1,3- or 1,4-bis(isocyanatomethyl) cyclohexane) ($H_6$XDI).

These polyisocyanate monomers may be used singly or in combination of two or more.

Examples of the polyisocyanate derivative include multimers (e.g., dimer, trimer (e.g., isocyanurate-modified product), pentamer, septamer, etc.), an allophanate-modified product (e.g., allophanate-modified product produced by reaction of the above-described polyisocyanate monomer with the low-molecular-weight polyol to be described later, etc.), a polyol modified product (e.g., polyol modified product (alcohol adduct) produced by reaction of polyisocyanate monomer with a low-molecular-weight polyol to be described later etc.), a biuret-modified product (e.g., biuret-modified product produced by reaction of the above-described polyisocyanate monomer with water and amines etc.), a urea-modified product (e.g., urea-modified product produced by reaction of the above-described polyisocyanate monomer with diamine etc.), an oxadiazinetrione-modified product (e.g., oxadiazinetrione produced by reaction of the above-described polyisocyanate monomer with carbon dioxide etc.), a carbodiimide-modified product (carbodiimide-modified product produced by decarboxylation condensation reaction of the above-described polyisocyanate monomer etc.), a urethodione-modified product, and a uretonimine-modified product of the above-described polyisocyanate monomer. Furthermore, examples of the polyisocyanate derivative also include polymethylenepolyphenylpolyisocyanate (crude MDI, polymeric MDI).

These polyisocyanate derivatives may be used singly or in combination of two or more.

These polyisocyanate components may be used singly or in combination of two or more.

For the polyisocyanate component, preferably, polyisocyanate monomer is used, more preferably, alicyclic polyisocyanate is used, even more preferably, methylenebis(cyclohexyl isocyanate), bis(isocyanatomethyl) cyclohexane are used, and particularly preferably, bis(isocyanatomethyl) cyclohexane is used.

When the polyisocyanate component contains bis(isocyanatomethyl) cyclohexane, strength and stain resistance of the eyewear can be improved.

When the polyisocyanate component contains bis(isocyanatomethyl) cyclohexane, for example, 5 parts by mass or more, preferably 20 parts by mass or more, more preferably 50 parts by mass or more, further preferably 70 parts by mass or more, and particularly preferably 100 parts by mass (that is, the polyisocyanate component consists only of bis(isocyanatomethyl) cyclohexane) of bis(isocyanatomethyl) cyclohexane relative to 100 parts by mass of the polyisocyanate component is contained.

When the bis(isocyanatomethyl) cyclohexane is contained in the above-described range, strength and stain resistance of eyewear can be improved.

Furthermore, bis(isocyanatomethyl) cyclohexane includes structural isomers of 1,2-bis(isocyanatomethyl) cyclohexane, 1,3-bis(isocyanatomethyl) cyclohexane, and 1,4-bis(isocyanatomethyl) cyclohexane.

For the bis(isocyanatomethyl) cyclohexane, preferably 1,3-bis(isocyanatomethyl) cyclohexane, 1,4-bis(isocyanatomethyl) cyclohexane are used, and more preferably 1,4-bis(isocyanatomethyl) cyclohexane is used.

Use of 1,4-bis(isocyanatomethyl) cyclohexane allows for improvement in strength, bending resistance, stain resistance, and mold processability of the eyewear.

When the polyisocyanate component contains 1,4-bis (isocyanatomethyl) cyclohexane, for example, 5 parts by mass or more, preferably 20 parts by mass or more, more preferably 50 parts by mass or more, further preferably 80 parts by mass or more, particularly preferably 100 parts by mass (that is, the polyisocyanate component consists only of 1,4-bis(isocyanatomethyl) cyclohexane) of 1,4-bis(isocyanatomethyl) cyclohexane relative to 100 parts by mass of the polyisocyanate component is contained.)

When the 1,4-bis(isocyanatomethyl) cyclohexane is contained in the above-described range, strength, mold processability, bending resistance, and stain resistance of the eyewear can be improved.

The 1,4-bis(isocyanatomethyl) cyclohexane includes stereoisomers of cis-1,4-bis(isocyanatomethyl) cyclohexane (hereinafter referred to as cis 1,4 isomer) and trans-1,4-bis (isocyanatomethyl) cyclohexane (hereinafter referred to as trans 1,4 isomer).

When the 1,4-bis(isocyanatomethyl) cyclohexane is used, for example, 70 mol % or more, preferably 80 mol % or more, more preferably 82 mol % or more, and for example, less than 97 mol %, preferably less than 93 mol %, more preferably less than 87 mol % of the trans 1,4 isomer is contained relative to a total amount of cis 1,4 isomer and trans 1,4 isomer in the 1,4-bis(isocyanatomethyl) cyclohexane. The cis 1,4 isomer is contained, for example, more than 3 mol %, preferably more than 7 mol %, more preferably more than 13 mol %, and for example, 30 mol % or less, preferably 20 mol % or less, more preferably 18 mol % or less.

When the trans isomer content and the cis isomer content in the 1,4-bis(isocyanatomethyl) cyclohexane are in the above-described range, strength, mold processability, and stain resistance of the eyewear can be improved.

The active hydrogen group-containing component is a compound having an active hydrogen group (e.g., hydroxyl group, amino group, etc.), and for example, a polyol component and a polyamine component are used.

Examples of the polyol component include low-molecular-weight polyols and high-molecular weight polyols.

The low-molecular-weight polyol is a compound having two or more hydroxyl groups and a number average molecular weight of 40 or more and less than 300, preferably less than 400, and examples thereof include dihydric alcohols such as ethylene glycol, propylene glycol, 1,3-propanediol, 1,4-butanediol, 1,3-butanediol, 1,2-butanediol, 1,5-pentanediol, 1,6-hexanediol, neopentyl glycol, 3-methyl-1,5-pentanediol, 2,2,2-trimethylpentanediol, 3,3-dimethylolheptane, alkane (C7 to 20) diol, 1,3- or 1,4-cyclohexanedimethanol, and a mixture thereof, 1,3- or 1,4-cyclohexanediol and a mixture thereof, hydrogenated bisphenol A, 1,4-dihydroxy-2-butene, 2,6-dimethyl-1-octene-3,8-diol, bisphenol A, diethylene glycol, triethylene glycol, dipropylene glycol, and isosorbide; trihydric alcohols such as glycerin, trimethylolpropane, and triisopropanolamine; tetrahydric alcohols such as tetramethylolmethane (pentaerythritol), and diglycerol; pentahydric alcohols such as xylitol; hexahydric alcohols such as sorbitol, mannitol, allitol, iditol, dulcitol, altritol, inositol, and dipentaerythritol; heptahydric alcohols such as perseitol; and octahydric alcohols such as sucrose.

These low-molecular-weight polyols may be used singly or in combination of two or more.

For the low-molecular-weight polyol, in view of improvement in strength, bending resistance, and stain resistance of eyewear, preferably dihydric alcohols are used, more preferably 1,3-propanediol, 1,4-butanediol, and 1,6-hexanediol are used, more preferably 1,3-propanediol and 1,4-butanediol are used, further preferably 1,4-butanediol is used.

The high-molecular weight polyol is a compound having two or more hydroxyl groups and having a number average molecular weight of 300 or more, preferably 400 or more and 5000 or less, preferably 3000 or less, and examples thereof include polyether polyol, polyester polyol, polycarbonate polyol, polyurethane polyol, epoxy polyol, vegetable oil-based polyol, polyolefin polyol, acrylic polyol, silicone polyol, fluorine polyol, and vinyl monomer-modified polyol.

Examples of the polyether polyol include polyalkylene (C2 to 3) polyol and polytetramethylene ether polyol.

Examples of the polyalkylene (C2 to 3) polyol include adduct polymer of alkylene oxide (including random and/or block copolymer of two or more types of alkylene oxides) such as ethylene oxide, propyleneoxide, and trimethyleneoxide in which the above-described low-molecular-weight polyol or the polyamine component (described later) is used as the initiator. To be specific, polyalkylene polyol includes, for example, polyethylene glycol, polypropylene glycol, ethylene oxide-propylene oxide copolymer (random and/or block copolymer), and polytrimethylene ether glycol.

Examples of the polytetramethylene ether polyol include polytetramethylene ether glycol, to be specific, examples thereof include a ring-opening polymerization product produced by cationic polymerization of tetrahydrofuran, and noncrystalline polytetramethylene ether glycol produced by copolymerizing the polymerization unit of tetrahydrofuran with the above-described low-molecular-weight polyol (dihydric alcohol).

Examples of the polyether polyol include plant derived polyether polyol, to be specific, plant derived polyalkylene (C2 to 3) polyol produced by using plant derived low-molecular-weight polyols, i.e., 1,3-propanediol, 1,4-butanediol, 1,3-butanediol, isosorbide, glycerin, sorbitol, and sucrose as an initiator; and plant derived polytetramethylene ether glycol produced by ring-opening polymerization of tetrahydrofuran using furfural derived from a plant derived material such as corn as the material.

Such plant derived polyether polyols can be obtained as commercially available products, and examples thereof include PTG2000SN (P)(polytetramethylene ether glycol in which biomass material is used, manufactured by Hodogaya Chemical Co., LTD. number average molecular weight 2000), and PTG1000SN (P)(polytetramethylene ether glycol in which biomass material is used, manufactured by Hodogaya Chemical Co., LTD. number average molecular weight 1000).

Furthermore, examples of the plant derived polyether polyols include polytrimethylene ether polyol produced by polycondensation reaction of plant derived 1,3-propanediol produced by fermentation process of plants such as corns.

Such plant-derived polyether polyols can be obtained as commercially available products as well, and examples thereof include selenol H1000 (polytrimethylene ether polyol in which biomass material is used, Dupont, number average molecular weight 1000), and selenol H2000 (polytrimethylene ether polyol in which biomass material is used, Dupont, number average molecular weight 2000).

Examples of the polyester polyol include a polycondensation product obtained by allowing the above-described low-molecular-weight polyol and polybasic acid to react under known conditions.

Examples of the polybasic acid include saturated aliphatic dicarboxylic acids such as oxalic acid, malonic acid, succinic acid, methylsuccinic acid, glutaric acid, adipic acid, 1,1-dimethyl-1,3-dicarboxypropane, 3-methyl-3-ethylglutaric acid, azelaic acid, sebacic acid, saturated aliphatic dicarboxylic acids (C 11 to 13), etc.; unsaturated aliphatic dicarboxylic acids such as maleic acid, fumaric acid, itaconic acid, etc.; aromatic dicarboxylic acids such as orthophthalic acid, isophthalic acid, terephthalic acid, toluenedicarboxylic acid, naphthalenedicarboxylic acid, etc.; alicyclic dicarboxylic acids such as hexahydrophthalic acid, etc.; other carboxylic acids such as dimer acid, hydrogenated dimer acid, het acid, etc. and acid anhydrides derived from these carboxylic acids such as oxalic anhydride, succinic anhydride, maleic anhydride, phthalic anhydride, 2-alkyl (C 12 to C 18) succinic anhydride, tetrahydrophthalic anhydride, trimellitic anhydride, and hallides derived from carboxylic acids thereof such as oxalyl dichloride, adipoyl dichloride, and sebacoyl dichloride.

Examples of the polyester polyol include plant derived polyester polyol, to be specific, vegetable oil polyester polyols obtained by condensation reaction of hydroxycarboxylic acid such as hydroxyl group-containing vegetable oil fatty acid (e.g., castor oil fatty acid containing ricinoleic acid, hydrogenated castor oil fatty acid containing 12-hydroxystearic acid, etc.) using the above-described low-molecular-weight polyol as an initiator under known conditions.

Examples of the polyester polyol include polycaprolactone polyol, and polyvalerolactone polyol obtained by ring-opening polymerization of lactones such as $\Sigma$-caprolactone, $\gamma$-valerolactone, etc. and lactides such as L-lactide, D-lactide using the above-described low-molecular-weight polyols (preferably, dihydric alcohol) as an initiator; and further lactone-based polyester polyols obtained by copolymerizing such a polycaprolactone polyol or polyvalerolactone polyol with the above-described dihydric alcohol.

Examples of the polycarbonate polyol include a ring-opening polymerization product of ethylene carbonate using the above-mentioned low-molecular-weight polyol (preferably dihydric alcohol) as an initiator; and amorphous polycarbonate polyol obtained by copolymerizing a ring-opening polymerization product and dihydric alcohol such as 1,4-butanediol, 1,5-pentanediol, 3-methyl-1,5-pentanediol, or 1,6-hexandiol.

Examples of the polycarbonate polyol include plant derived polycarbonate polyols, to be specific, alicyclic dihydroxy compounds such as isosorbide derived from glucose, a plant derived material, and polycarbonate polyol produced by transesterification of the above-described low molecular-weight polyol (preferably dihydric alcohol) with diphenyl carbonate.

Polyurethane polyols can be obtained as polyester polyurethane polyol, polyether polyurethane polyol, polycarbonate polyurethane polyol, or polyester polyether polyurethane polyol, by allowing polyester polyol, polyether polyol and/or polycarbonate polyol obtained as described above to react with polyisocyanate at an equivalent ratio (OH/NCO) of hydroxyl group (OH) to isocyanate group (NCO) of more than 1.

Examples of the epoxy polyol include epoxy polyol obtained by a reaction between the above-mentioned low-molecular-weight polyol and a polyfunctional halohydrin such as epichlorohydrin and β-methyl epichlorohydrin.

Examples of the vegetable oil polyol include vegetable derived oil polyol, to be more specific, examples thereof include hydroxyl group-containing vegetable oils such as castor oil and coconut oil. Examples thereof include ester-modified castor oil polyol obtained by reaction of castor oil polyol or castor oil fatty acid with polypropylene polyol.

Examples of the polyolefin polyol include polybutadiene polyol and partially saponified ethylene-vinylacetate copolymer.

Examples of the acrylic polyol include copolymers obtained by copolymerizing hydroxyl group-containing acrylate with a copolymerizable vinyl monomer copolymerizable with the hydroxyl group-containing acrylate.

Examples of the hydroxyl group-containing acrylate include 2-hydroxyethyl (meth)acrylate, hydroxypropyl (meth)acrylate, hydroxybutyl (meth)acrylate, 2,2-dihydroxymethylbutyl (meth)acrylate, polyhydroxyalkyl maleate, and polyhydroxyalkyl fumarate. Preferably, 2-hydroxyethyl (meth)acrylate is used.

Examples of the copolymerizable vinyl monomer include alkyl (meth)acrylate (having 1 to 12 carbon atoms) such as methyl (meth)acrylate, ethyl (meth)acrylate, propyl (meth)acrylate, isopropyl (meth)acrylate, butyl (meth)acrylate, isobutyl (meth)acrylate, s-butyl (meth)acrylate, t-butyl (meth)acrylate, pentyl (meth)acrylate, isopentyl (meth)acrylate, hexyl (meth)acrylate, isononyl (meth)acrylate, isobornyl (meth)acrylate, 2-ethylhexyl (meth)acrylate, and cyclohexylacrylate; aromatic vinyls such as styrene, vinyltoluene, and α-methylstyrene; vinyl cyanide such as (meth) acrylonitrile; vinyl monomers having a carboxyl group such as (meth) acrylic acid, fumaric acid, maleic acid, and itaconic acid, or alkylester thereof; alkane polyol poly (meth)acrylate such as ethylene glycol di(meth)acrylate, butyleneglycol di(meth)acrylate, hexanediol di(meth)acrylate, oligoethylene glycol di(meth)acrylate, trimethylolpropane di(meth) acrylate, and trimethylolpropanetri (meth)acrylate; and vinyl monomers containing isocyanate groups such as 3-(2-isocyanate-2-propyl)-α-methylstyrene.

The acrylic polyol can be obtained by copolymerizing these hydroxyl group-containing acrylates and copolymerizable vinyl monomers in the presence of a suitable solvent and a suitable polymerization initiator.

Examples of the acrylic polyol include silicone polyol and fluorine polyol.

Examples of the silicone polyol include acrylic polyol in which a silicone compound containing vinyl group such as for example, γ-methacryloxypropyltrimethoxysilane is blended in the above-described copolymerization of acrylic polyol as a copolymerizable vinyl monomer, and polysiloxanes having molecule ends modified with alcohol (poly di C1-6 alkylsiloxane such as polydimethylsiloxane, etc.).

Examples of the fluorine-containing polyol include acrylic polyols blended with a fluorine-containing compound containing a vinyl group such as tetrafluoroethylene or chlorotrifluoroethylene, as a copolymerizable vinyl monomer in the copolymerization of the acrylic polyol.

The vinyl monomer-modified polyol can be obtained by a reaction between the above-mentioned high-molecular-weight polyol and a vinyl monomer.

Such a high-molecular weight polyol has a number average molecular weight of, for example, 400 or more, preferably 800 or more, and for example, 5000 or less, preferably 3000 or less.

These high-molecular weight polyols may be used singly or in combination of two or more.

In view of improvement in durability and contact of eyewear, preferably, polyether polyol, more preferably, polytrimethylene ether glycol, polytetramethylene ether glycol, even more preferably, plant derived polytetramethylene ether glycol is used for the high-molecular weight polyol.

The polyamine component is a compound having two or more amino groups, and examples thereof include aromatic polyamine, aralkyl polyamine, alicyclic polyamine, aliphatic polyamine, amino alcohol, an alkoxysilyl compound having a primary amino group, or a primary amino group and a secondary amino group, and polyoxyethylene group-containing polyamine.

Examples of the aromatic polyamine include 4,4'-diphenylmethanediamine, tolylenediamine, diethyltoluenediamine (trade name: ETHACURE® 100, manufactured by ALBEMARLE JAPAN CORPORATION) and a mixture of 1-methyl-3,5-bis(methylthio)-2,4 and 2,6-diaminobenzene (trade name: ETHACURE® 300, manufactured by ALBEMARLE JAPAN).

Examples of the aralkyl polyamine include 1,3- or 1,4-xylylene diamine, or mixtures thereof.

Examples of the alicyclic polyamine include 3-aminomethyl-3,5,5-trimethylcyclohexylamine (also called: isophoronediamine), 4,4'-dicyclohexylmethanediamine, 2,5 (2,6)-bis(aminomethyl) bicyclo[2.2.1]heptane, 1,4-cyclohexanediamine, 1-amino-3-aminomethyl-3,5,5-trimethylcyclohexane, bis-(4-aminocyclohexyl) methane, diaminocyclohexane, 3,9-bis(3-aminopropyl)-2,4,8,10-tetraoxaspiro [5,5]undecane, and 1,3- and 1,4-bis(aminomethyl) cyclohexane and a mixture thereof.

Examples of the aliphatic polyamine include ethylenediamine, propylene diamine, 1,3-propane diamine, 1,4-butanediamine, 1,5-pentanediamine, 1,6-hexamethylenediamine, hydrazine (including hydrate), diethylenetriamine, triethylenetetramine, tetraethylenepentamine, and 1,3-diaminopentane.

Examples of the amino alcohol include N-(2-aminoethyl) ethanolamine.

Examples of the alkoxysilyl compounds having a primary amino group, or having a primary amino group and a secondary amino group include alkoxysilyl group-containing monoamines such as γ-aminopropyltriethoxysilane and N-phenyl-γ-aminopropyl trimethoxysilane, N-β (aminoethyl) γ-aminopropyl trimethoxysilane, and N-β (aminoethyl) γ-aminopropylmethyl dimethoxysilane.

Examples of the polyoxyethylene group-containing polyamine include polyoxyalkylene etherdiamine such as polyoxyethylene etherdiamine. More specific examples thereof include diamine PEG#1000 manufactured by NOF Corporation, and Jeffamine ED-2003, EDR-148, and XTJ-512 manufactured by Huntsman Corporation.

These polyamine components may be used singly or in combination of two or more.

These active hydrogen group-containing components may be used singly or in combination of two or more. For the active hydrogen group-containing component, preferably, the polyol component is used, more preferably, the low-molecular-weight polyol is used in combination with the high-molecular weight polyol.

For the active hydrogen group-containing component, preferably, a biomass material-derived active hydrogen group-containing component is used.

Examples of the biomass material-derived active hydrogen group-containing component include biomass material-derived polyol components such as plant derived polytetramethylene ether polyol, plant derived polyesterpolyol, plant derived polycarbonate polyol, and plant derived oil polyol.

The biomass material-derived active hydrogen group-containing component is not limited to the above-described examples, and various biomass material-derived active hydrogen group-containing components may be used.

The thermoplastic polyurethane produced by using these biomass material-derived polyisocyanate components and biomass material-derived active hydrogen group-containing components can substantially reduce the amount of carbon dioxide discharge at the time of combustion, and lessen the burden on earth environment.

When the thermoplastic polyurethane is produced by using a biomass material, the biobased content is, for example, 5% or more, preferably 25% or more, more preferably 40% or more, further preferably 50% or more.

The biobased content can be determined in conformity with the standard of ASTM D6866 METHOD-B.

The thermoplastic polyurethane can be produced, for example, by polymerization method such as bulk polymerization and solution polymerization.

In bulk polymerization, for example, while stirring one of the polyisocyanate component and the active hydrogen group-containing component, the other is added thereto under nitrogen flow, and reaction is performed at a reaction temperature of 50 to 250° C., even more preferably 50 to 200° C., for about 0.5 to 25 hours.

In solution polymerization, the polyisocyanate component, and the active hydrogen group-containing component are added to an organic solvent, and reaction is performed at a reaction temperature of 50 to 120° C., preferably 50 to 100° C., for about 0.5 to 15 hours.

Examples of the organic solvent include ketones such as acetone, methyl ethyl ketone, methyl isobutyl ketone, and cyclohexanone; nitriles such as acetonitrile; alkyl esters such as methyl acetate, ethyl acetate, butyl acetate, and isobutyl acetate; aliphatic hydrocarbons such as n-hexane, n-heptane, and octane; alicyclic hydrocarbons such as cyclohexane and methylcyclohexane; aromatic hydrocarbons such as toluene, xylene, and ethylbenzene; glycol ether esters such as methyl cellosolve acetate, ethyl cellosolve acetate, methyl carbitol acetate, ethyl carbitol acetate, ethylene glycol ethyl ether acetate, propylene glycol methyl ether acetate, 3-methyl-3-methoxy butyl acetate, and ethyl-3-ethoxy propionate; ethers such as diethyl ether, tetrahydrofuran, and dioxane; halogenated aliphatic hydrocarbons such as methyl chloride, methylene chloride, chloroform, carbon tetrachloride, methyl bromide, methylene iodide, and dichloroethane; and aprotic polar solvents such as N-methylpyrrolidone, dimethylformamide, N,N'-dimethyl acetamide, dimethyl sulfoxide, and hexamethyl phosphoramide.

Examples of the organic solvent also include nonpolar solvents (nonpolar organic solvents), and examples of the nonpolar solvent include those nonpolar organic solvents having an aniline point of, for example, 10 to 70° C., preferably 12 to 65° C. and having low toxicity and solvency, such as aliphatic, naphthene hydrocarbon organic solvent; and vegetal oils typically represented by turpentine oil.

The nonpolar organic solvents can be obtained from commercially available products, and examples of those commercially available products include petroleum hydrocarbon organic solvents such as Haws (manufactured by Shell Chemicals, aniline point 15° C.), Swasol 310 (manufactured by Maruzen Petrochemical, aniline point 16° C.), Esso Naphtha No. 6 (manufactured by Exxon Mobil Chemical, aniline point 43° C.), Laws (manufactured by Shell Chemicals, aniline point 43° C.), Esso Naphtha No. 5 (manufactured by Exxon Mobil Corporation, aniline point 55° C.), and pegasol 3040 (manufactured by Exxon Mobil Corporation, aniline point 55° C.); and also turpentine oils such as methylcyclohexane (aniline point 40° C.), ethylcyclohexane (aniline point 44° C.), and gum turpentine N (manufactured by YASUHARA CHEMICAL CO., LTD., aniline point 27° C.).

The mixing ratio of the organic solvent is set suitably in accordance with the purpose and application.

Furthermore, in the above-described polymerization reaction, as necessary, for example, a known urethanizing catalyst such as amines and organometallic compounds can be added.

Examples of the amines include tertiary amines such as triethylamine, triethylenediamine, bis-(2-dimethylaminoethyl) ether, and N-methylmorpholine; quaternary ammonium salts such as tetraethyl hydroxyl ammonium; and imidazoles such as imidazole and 2-ethyl-4-methylimidazole.

Examples of the organometallic compound include organotin compounds such as tin acetate, tin octylate, tin oleate, tin laurate, dibutyl tin diacetate, dimethyl tin dilaurate, dibutyl tin dilaurate, dibutyl tin dimercaptide, dibutyl tin maleate, dibutyl tin dilaurate, dibutyl tin dineodecanoate, dioctyl tin dimercaptide, dioctyl tin dilaurylate, and dibutyl tin dichloride; organic lead compounds such as lead octanoate and lead naphthenate; organic nickel compounds such as nickel naphthenate; organic cobalt compounds such as cobalt naphthenate; organocopper compounds such as octenate copper; and organic bismuth compounds such as bismuth octylate and bismuth neodecanoate.

Examples of the urethanizing catalysts also include potassium salts such as potassium carbonate, potassium acetate, and potassium octoate.

These urethanizing catalysts may be used singly or in combination of two or more.

For the urethanizing catalyst, preferably, organometallic compound, more preferably, tin octylate is used.

The mixing ratio of the urethanizing catalyst is set suitably in accordance with the purpose and application.

In bulk polymerization and solution polymerization, for example, the polyisocyanate component and the active hydrogen group-containing component are blended so that the equivalent ratio (NCO/active hydrogen group) of the isocyanate group in the polyisocyanate component relative to the active hydrogen group (hydroxyl group, amino group) in the active hydrogen group-containing component is, for example, 0.75 or more, preferably 0.9 or more, more preferably 0.95 or more, for example, 1.3 or less, preferably 1.1 or less, more preferably 1.05 or less.

When the above-described polymerization reaction is performed more industrially, thermoplastic polyurethane can be produced by, for example, a known method such as one-shot method and prepolymer method.

In one-shot method, for example, the polyisocyanate component and the active hydrogen group-containing component are formulated (mixed) such that the equivalent ratio (NCO/active hydrogen group) of the isocyanate group in the polyisocyanate component relative to the active hydrogen group (hydroxyl group, amino group) in the active hydrogen group-containing component is, for example, 0.75 or more, preferably 0.9 or more, more preferably 0.95 or more, and for example, 1.3 or less, preferably 1.1 or less, more preferably 1.05 or less, and curing reaction is performed at, for example, room temperature to 250° C., preferably, room temperature to 200° C., and for example, 5 minutes to 72 hours, preferably 4 to 24 hours. The curing temperature may be constant, or can also be gradually increased or cooled.

In the prepolymer method, for example, first, the polyisocyanate component is allowed to react with a portion of the active hydrogen group-containing component (preferably, high-molecular weight polyol) to synthesize an isocyanate group-terminated prepolymer having isocyanate group at its molecular terminal. Then, the produced isocyanate group-terminated prepolymer is allowed to react with the remaining portion of the active hydrogen group-containing component (preferably, low-molecular-weight polyol, polyamine component) to perform a chain extension reaction. Therefore, the remaining portion of the active hydrogen group-containing component is used as a chain extender in the prepolymer method.

To synthesize the isocyanate group-terminated prepolymer, the polyisocyanate component and a portion of the active hydrogen group-containing component are formulated (mixed) so that the equivalent ratio (NCO/active hydrogen group) of the isocyanate group in the polyisocyanate component relative to the active hydrogen group in the portion of the active hydrogen group-containing component is, for example, 2 or more, preferably 3 or more, more preferably 4 or more, further preferably 5 or more, for example, 25 or less, preferably 10 or less, more preferably 8 or less, further preferably 7 or less, and reaction is performed in a reaction vessel at, for example, room temperature to 150° C., preferably 50 to 120° C., and for example, 0.5 to 18 hours, preferably 2 to 10 hours. In this reaction, as necessary, the above-described urethanizing catalyst may be added.

Then, to allow the obtained isocyanate group-terminated prepolymer to react with the remaining portion of the active hydrogen group-containing component (chain extender), the isocyanate group-terminated prepolymer and the remaining portion of the active hydrogen group-containing component are formulated (mixed) so that the equivalent ratio (NCO/active hydrogen group) of the isocyanate group in the isocyanate group-terminated prepolymer relative to the active hydrogen group in the remaining portion of the active hydrogen group-containing component is, for example, 0.75 to 1.3, preferably 0.9 to 1.1, and for example, the mixture is allowed to react at 100 to 200° C., for example, 0.1 to 24 hours, and thereafter, further allowed to react at 60 to 150° C., for example, for 1 to 48 hours. After the reaction, as necessary, aging at room temperature to 80° C. for about 1 to 10 days can be carried out.

When using solvent polymerization, preferably, the organic solvent is removed by a known removal means such as distillation and extraction before injecting the thermoplastic polyurethane into a mold.

The thermoplastic polyurethane can be produced in this manner.

The thus produced thermoplastic polyurethane has a hard segment concentration of, for example, 15 mass % or more, preferably 25 mass % or more, more preferably 30 mass % or more, further preferably 35 mass % or more, and for example, 95 mass % or less, preferably 70 mass % or less, more preferably 60 mass % or less, further preferably less than 60 mass %, particularly preferably 50 mass % or less.

The hard segment concentration can be calculated, for example, when prepolymer method is used, from the mixing formulation (charged amount) of the components based on the following formula. [chain extender (g)+(chain extender (g)/molecular weight of chain extender (g/mol))×average molecular weight of polyisocyanate component (g/mol)]÷(polyisocyanate component (g)+active hydrogen group-containing component (g))×100 The hard segment concentration can also be measured by, for example, subjecting the thermoplastic polyurethane to solid-state NMR or solution NMR measurement. Specific measurement methods are described in, for example, Satoshi Yamasaki et. al "Effect of aggregation structure on rheological properties of thermoplastic polyurethanes" Polymer, vol 48, pages 4793 to 4803, 2007.

The hard segment concentration calculated by the above-described formula and the hard segment concentration measured by NMR measurement of the above-described method may have a gap of about, for example, −10 mass % to +10 mass %.

In the present invention, the hard segment concentration represents a calculated value based on the above-described formula unless otherwise mentioned.

When the hard segment concentration of the thermoplastic polyurethane is within the above-described range, the tan δ peak temperature can be adjusted to be in a predetermined range to be described later.

The hard segment concentration of the thermoplastic polyurethane can be adjusted by equivalent ratio (NCO/active hydrogen group) at the time of reaction of the polyisocyanate component and the active hydrogen group-containing component.

To be more specific, for example, when prepolymer method is used, by setting the equivalent ratio (NCO/active hydrogen group) at the time of synthesizing the isocyanate group-terminated prepolymer to 2 or more, preferably 3 or more, and 25 or less, preferably 10 or less, and the hard segment concentration to 15 mass % or more, preferably 25 mass % or more, and 95 mass % or less, preferably 70 mass % or less, the tan δ peak temperature can be adjusted to be in the above-described range at both a relatively low temperature side and a relatively high temperature side.

Furthermore, by setting the equivalent ratio (NCO/active hydrogen group) at the time of synthesizing the isocyanate group-terminated prepolymer to 4 or more, preferably 5 or more, and 8 or less, preferably 7 or less, the hard segment concentration can be adjusted to 30 mass % or more, preferably 35 mass % or more, and less than 60 mass %, and the tan δ peak temperature at the relatively high temperature side can be set to less than 50° C.

Preferably, the eyewear material contains, as an additive, acryl-modified organopolysiloxane.

The acryl-modified organopolysiloxane is produced by copolymerizing, for example, organopolysiloxane and (meth)acrylate.

Organopolysiloxane has a radical polymerization group at its molecular terminal, to be specific, is a compound represented by general formula (1) below.

[Chem. 1]
Chem. 1

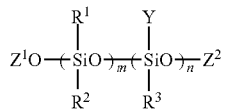

(1)

(in formula (1), $R^1$, $R^2$, and $R^3$ independently represents a hydrocarbon group having 1 to 20 carbon atoms or a halogenated hydrocarbon group, Y represents a monovalent radical polymerization group, $Z^1$ and $Z^2$ independently represent hydrogen, a lower alkyl group having 1 to 4 carbon atoms, or a group represented by formula-$SiR^4R^5R^6$. In the above-described formula, $R^4$ and $R^5$ independently represent the monovalent hydrocarbon group having 1 to 20 carbon atoms or a halogenated hydrocarbon group represented in the above-described $R^1$ to $R^3$, and $R^6$ represents the above-described monovalent hydrocarbon group having 1 to 20 carbon atoms or a halogenated hydrocarbon group given as examples in $R^1$ to $R^3$, or a radical reactive group. "m" represents a positive integer of 10000 or less, and n represents an integer of 1 or more.) Examples of the above-described hydrocarbon group having 1 to 20 carbon atoms represented by $R^1$, $R^2$, and $R^3$ in general formula (1) include alkyl groups such as methyl, ethyl, propyl, and butyl, aryl groups such as phenyl, tolyl, xylyl, and naphthyl; and aralkyl group such as benzyl.

Examples of the halogenated hydrocarbon group having 1 to 20 carbon atoms represented by $R^1$, $R^2$, and $R^3$ include a group in which at least one of hydrogen atoms bonded to the carbon atoms of the above-described hydrocarbon group having 1 to 20 carbon atoms is replaced with, for example, halogen atoms such as chlorine and fluorine.

In the above-described general formula (1), examples of the monovalent radical polymerization group represented by Y include vinyl, allyl, and γ-(meth) acryloyloxy propyl.

In the above-described general formula (1), examples of the lower alkyl group having 1 to 4 carbon atoms represented by $Z^1$ and $Z^2$ include methyl, ethyl, propyl, and butyl.

"m" is preferably a positive integer satisfying formula (2) below.

$$500 \leq m \leq 8000 \quad (2)$$

"n" is preferably a positive integer satisfying formula (3) below.

$$1 \leq n \leq 500 \quad (3)$$

In the above-described general formula (1), the siloxane chain represented by —$(Si(R^1)(R^2)O)m$- and —$(Si(R^3)(Y)O)n$- can be straight or branched.

(Meth)acrylate is methacrylic acid ester (methacrylate) and/or acrylic acid ester (acrylate), to be specific, examples thereof include alkyl (meth)acrylates such as methyl (meth)acrylate, ethyl (meth)acrylate, propyl (meth)acrylate, isopropyl (meth)acrylate, butyl (meth)acrylate, isobutyl (meth) acrylate, tert-butyl (meth)acrylate, pentyl (meth)acrylate, hexyl (meth)acrylate, octyl (meth)acrylate, 2-ethylhexyl (meth)acrylate, lauryl (meth)acrylate, and stearyl (meth) acrylate; alkoxyalkyl (meth)acrylate such as methoxyethyl (meth)acrylate and butoxyethyl (meth)acrylate; cycloalkyl (meth)acrylate such as cyclohexyl (meth)acrylate; and aryl (meth)acrylate such as phenyl (meth)acrylate.

These (meth)acrylates may be used singly, or may be used in combination of two or more.

In addition to the above-described components, a copolymerizable monomer that is copolymerizable with (meth) acrylate can also be used in combination.

Examples of the copolymerizable monomer include polyfunctional ethylenically unsaturated monomer or monofunctional ethylenically unsaturated monomer.

Examples of the polyfunctional ethylenically unsaturated monomer include unsaturated amide and alkylol or alkoxyalkyl of unsaturated amide such as (meth) acrylamide, diacetone (meth) acrylamide, N-methylol (meth) acrylamide, N-butoxymethyl (meth) acrylamide, and N-methoxymethyl (meth) acrylamide; oxirane group-containing unsaturated monomers such as glycidyl (meth)acrylate and glycidylallylether; hydroxyl group-containing unsaturated monomers such as 2-hydroxyethyl (meth)acrylate and 2-hydroxypropyl (meth)acrylate; carboxyl group-containing unsaturated monomers such as for example, (meth) acrylic acid, maleic anhydride, crotonic acid, and itaconic acid; amino group-containing unsaturated monomers such as N-dimethylaminoethyl (meth)acrylate and N-diethylaminoethyl (meth)acrylate; polyalkyleneoxide group-containing unsaturated monomers such as ethyleneoxide or propylene oxide adduct of (meth) acrylic acid; ester of polyhydric alcohol and (meth) acrylic acid such as ethylene glycol di(meth)acrylate, diethylene glycol di(meth)acrylate, and trimethylolpropanetri (meth)acrylate; and allyl (meth)acrylate and divinylbenzene.

Examples of the monofunctional ethylenically unsaturated monomers include styrene, α-methylstyrene, vinyltoluene, acrylonitrile, vinyl chloride, vinylidene chloride, vinyl acetate, and vinyl propionate.

The mixing ratios in copolymerization of organopolysiloxane and (meth)acrylate are as follows: for example, 5 to 95 mass % of organopolysiloxane relative to a total amount of organopolysiloxane and (meth)acrylate, and for example, 5 to 95 mass % of (meth)acrylate relative to a total amount of organopolysiloxane and (meth)acrylate.

The acryl-modified organopolysiloxane is produced by a known polymerization method. To be specific, the acryl-modified organopolysiloxane is produced for example, by solution polymerization, emulsion polymerization, suspension polymerization, or dispersion polymerization. Preferably, the acryl-modified organopolysiloxane is produced by emulsion polymerization.

In emulsion polymerization, for example, organopolysiloxane and (meth)acrylate are emulsified by a known emulsifier, and thereafter a known radical polymerization initiator is added to allow graft copolymerization of organopolysiloxane with (meth)acrylate.

In emulsion polymerization, organopolysiloxane can be emulsified and/or polymerized with a known emulsifier, and then thereafter (meth)acrylate is graft copolymerized in the emulsion.

Furthermore, in emulsion polymerization, after organopolysiloxane is emulsified and/or polymerized by a known emulsifier in the presence of seed particles produced by polymerization of (meth) acrylate monomer, (meth)acrylate can be subjected to graft copolymerization in the emulsion.

Furthermore, by multistage polymerizing so as to allow organopolysiloxane to be core and (meth) acrylate ester polymer to be shell, acryl-modified organopolysiloxane having a core-shell structure (multilayer particles structure) can also be produced.

Acryl-modified organopolysiloxane can be produced in this manner.

The thus produced acryl-modified organopolysiloxane is prepared as particles, or emulsion dispersed in water.

The acryl-modified organopolysiloxane prepared as particles has an average particle size of, for example, 3 to 200 μm, preferably 5 to 60 μm, further preferably 10 to 45 μm.

The acryl-modified organopolysiloxane prepared as emulsion has a particle size of, for example, 10 to 1000 nm, preferably 50 to 600 nm, a viscosity at 20° C. of, for example, 1 to 5000 mPa·s, preferably 5 to 3500 mPa·s, further preferably 5 to 1000 mPa·s, and a solid content concentration of, for example, 5 to 70 mass %, preferably 20 to 65 mass %.

For the acryl-modified organopolysiloxane, a commercially available general product can be used, for example, such as Chaline series (trade name, manufactured by Nisshin Chemical Co., Ltd.).

To be more specific, for example, particles such as Chaline R-170S (average particle size 30 μm, manufactured by Nisshin Chemical Co., Ltd.) are used, and for example, emulsion such as Chaline R-170EM (solid content concentration 45 mass %, particle size 200 nm, manufactured by Nisshin Chemical Co., Ltd.) is used.

When the above-described acryl-modified organopolysiloxane is blended to the above-described thermoplastic polyurethane, the blending method is not particularly limited, and acryl-modified organopolysiloxane can be separately blended to the produced thermoplastic polyurethane, or in synthesis of thermoplastic polyurethane, acryl-modified organopolysiloxane can be blended along with the material components (polyisocyanate component, active hydrogen group-containing component, isocyanate group-terminated prepolymer, etc.). Preferably, in synthesis of thermoplastic polyurethane, acryl-modified organopolysiloxane is blended along with the material components (polyisocyanate component, active hydrogen group-containing component, isocyanate group-terminated prepolymer, etc.).

In the eyewear material, for example, 0.01 parts by mass or more, preferably 0.02 parts by mass or more, more preferably 0.04 parts by mass or more, further preferably 0.05 parts by mass or more, and for example, 1 part by mass or less, preferably 0.5 parts by mass or less, more preferably 0.2 parts by mass or less, particularly preferably 0.09 parts by mass or less of the acryl-modified organopolysiloxane is contained relative to 100 parts by mass of the thermoplastic polyurethane.

When the acryl-modified organopolysiloxane is contained relative to the thermoplastic polyurethane in the above-described range, fit can be improved.

In the eyewear material, as necessary, known additives such as plasticizers, anti-blocking agents, heat-resistant stabilizers, light stabilizers, ultraviolet ray absorbents, antioxidants, mold release agents, catalysts, and also pigments, dyes, lubricants, fillers, hydrolysis prevention agents can be further blended at a suitable ratio. These additives may be added at the time of synthesizing components, or may be added at the time of mixing and dissolving components, or may be added after the synthesis.

That is, eyewear material of the present invention is preferably consisting of the thermoplastic polyurethane and an additive (including acryl-modified organopolysiloxane).

The thus produced eyewear material has a hardness (in conformity with JIS K7311 (1995)) of, for example, Shore D30 or more, preferably, Shore D40 or more, more preferably, Shore D43 or more, even more preferably, Shore D45 or more, and for example, Shore D90 or less, preferably, Shore D85 or less.

The eyewear material has a specific gravity (in conformity with JIS Z8807 (2012)) of, for example, 0.8 or more, preferably 0.9 or more, more preferably 1.0 or more, and for example, 1.20 or less, preferably 1.15 or less.

The eyewear material has a strength at break (in conformity with JIS K7311 (1995)) of, for example, 25 MPa or more, preferably 30 MPa or more, more preferably 35 MPa or more, further preferably 40 MPa or more, and usually 80 MPa or less.

The eyewear material has an elongation at break (in conformity with JIS K7311 (1995)) of, for example, 100% or more, preferably 300% or more, more preferably 400% or more, and generally 800% or less.

The eyewear material has at least two tan δ peaks in dynamic viscoelasticity measurement using a dynamic viscoelasticity measuring apparatus under measurement conditions of a temperature increase speed of 5° C./min and a measurement frequency of 10 Hz with tensile mode.

The temperature (peak temperature) observed at the lowest temperature side of tan δ peak is less than 0° C., preferably less than −10° C., more preferably less than −20° C., even more preferably less than −30° C., particularly preferably, less than −40° C., and for example, −90° C. or more, preferably, −60° C. or more.

When the eyewear material has a tan δ peak in the above-described range, excellent contact can be achieved, and furthermore, excellent bending resistance can be achieved even in the low temperature region of less than 0° C.

The temperature (peak temperature) observed at the highest side of the tan δ peak is, 70° C. or less, preferably 60° C. or less, more preferably 50° C. or less, further preferably less than 50° C., and 0° C. or more, preferably 5° C. or more, more preferably 10° C. or more, further preferably 30° C. or more.

When the eyewear material has a tan δ peak in the above-described range, excellent fit can be produced.

The tan δ peak temperature depends on, as described above, the hard segment concentration, and the chemical structure of the thermoplastic polyurethane. The measurement method of the tan δ peak temperature is in conformity with Examples to be described later.

The eyewear material contains the above-described thermoplastic polyurethane as the main component, and therefore is excellent in processability and mechanical strength, and furthermore has a tan δ peak in dynamic viscoelasticity measurement at less than 0° C., and therefore excellent contact can be obtained, and furthermore, has a tan δ peak in dynamic viscoelasticity measurement at 0° C. or more and 70° C. or less, and therefore excellent in fit.

The eyewear material is lightweight and furthermore has excellent flexibility in molded article, which allows for excellent resilience even when stress deformed.

Therefore, the above-described eyewear material is suitably used in production of an eyewear frame, to be more specific, each part of an eyewear frame such as nose pads, earpiece (ear pads), temple (string portion), rim (lens surrounding), bridge (rim connecting portion), end piece (front both end portions), hinge (connecting portion between end piece and temple) of an eyewear.

The eyewear frame of the present invention is formed from the above-described eyewear material.

To be more specific, the eyewear frame can be produced by pelletizing the eyewear material (containing thermoplastic polyurethane as main component) produced as described above, and molding the eyewear material into a desired frame shape by a known molding method such as extrusion molding and injection molding.

For the eyewear frame molding, as necessary, along with the above-described eyewear material (including thermoplastic polyurethane as the main component), other thermoplastic resin may be used. Examples of other thermoplastic resin include thermoplastic polyamide described in Japanese Unexamined Patent Application Publication (Translation of PCT Application) 2010-534256, the blended resin of polyether-imide and polyphenylene ether sulfone described in Japanese Unexamined Patent Application Publication (Translation of PCT Application) 2010-532815, and polymethylpentene resin of commercially available products (trade name TPX series (manufactured by Mitsui Chemicals, Inc.), etc.), cyclic olefin copolymer (trade name Apel series (manufactured by Mitsui Chemicals, Inc.), etc.), and thermoplastic polyimide (trade name Aurum series (manufactured by Mitsui Chemicals, Inc.), etc.).

When these other thermoplastic resin is used, for example, an eyewear material containing the above-described thermoplastic polyurethane, and other thermoplastic resin (e.g., thermoplastic polyamide, etc.) are simultaneously injection molded, thereby composite molding an eyewear frame.

When the above-described eyewear material (including thermoplastic polyurethane as the main component) is used in combination with other thermoplastic resin, the mixing ratio of the eyewear material relative to a total amount of the eyewear material and other thermoplastic resin is, for example, 20 mass % or more, preferably 50 mass % or more, and for example, 90 mass % or less, preferably 70 mass % or less.

Furthermore, for example, a specific eyewear part is formed by using the above-described eyewear material (including the above-described thermoplastic polyurethane as the main component), and other eyewear parts are formed by using other thermoplastic resin.

To be more specific, the eyewear frame can be produced from a plurality of resins by using the above-described eyewear material (including the above-described thermoplastic polyurethane as the main component) for, for example, nose pads and earpiece (ear pads), and furthermore, using other thermoplastic resins (e.g., thermoplastic polyamide, etc.) for temple (string portion), and rim (lens surrounding).

The eyewear frame is preferably coated with a coating agent such as a polyurethane coating agent in view of appearance, solvent-resistant characteristics, and design.

The polyurethane coating agent is prepared, for example, as a two-part curing polyurethane resin composition which is used by blending the curing agent and the main component at the time of usage, mixing and blending them, and applied.

In the polyurethane coating agent, examples of the curing agent include, for example, the above-described polyisocyanate components (polyisocyanate components used for production of eyewear material), to be more specific, the above-described polyisocyanate monomer, and the above-described polyisocyanate derivative.

For the polyisocyanate component (curing agent) used as the polyurethane coating agent, preferably, aliphatic polyisocyanate is used, more preferably, pentamethylenediisocyanate and/or its derivative is used.

Use of the pentamethylenediisocyanate and/or its derivative allows for improvement in stain resistance and coating appearance of the eyewear.

For the pentamethylenediisocyanate, a preferable example include a biomass material-derived pentamethylenediisocyanate produced by allowing decarboxylation reaction of lysine, i.e., a biomass material, and converting amino group to isocyanate group in conformity with the method described in Examples in WO2011/108473.

In polyurethane coating agent, examples of the main component include the above-described polyol component (polyol component used in production of eyewear material), to be more specific, the above-described low-molecular-weight polyol, and the above-described high-molecular weight polyol.

For the polyol component (main component) used in the polyurethane coating agent, preferably, the above-described high-molecular weight polyol, more preferably, polyether polyol and acrylic polyol are used.

Use of these allows for improvement in stain resistance, coating appearance and surface contact of the eyewear.

For the polyol component (main component), preferably, polyether polyol and acrylic polyol are used in combination.

When polyether polyol and acrylic polyol are used in combination, the mixing ratio of the components is as follows: for example, 10 parts by mass or more, preferably 20 parts by mass or more, and for example, 70 parts by mass or less, preferably 50 parts by mass or less of the polyether polyol relative to 100 parts by mass of a total of the polyol component. The acrylic polyol is mixed, for example, 30 parts by mass or more, preferably 50 parts by mass or more, and for example, 90 parts by mass or less, preferably 80 parts by mass or less relative to 100 parts by mass of a total of the polyol component.

The polyurethane coating agent is used, by separately preparing the curing agent (polyisocyanate component) and the main component (polyol component), and they are blended at the time of usage, and mixed and stirred.

The curing agent (polyisocyanate component) and the main component (polyol component) are mixed at a ratio such that the equivalent ratio (NCO/OH) of the isocyanate group of the curing agent (polyisocyanate component) relative to the hydroxyl group of the main component (polyol component) is, for example, 0.5 to 5, preferably 0.6 to 3.

To one or both of the curing agent and the main component, as necessary, for example, additives such as epoxy resin, catalyst, coating improvement agent, leveling agent, antifoaming agent, stabilizers such as antioxidant and ultraviolet ray absorbent, plasticizer, surfactant, pigment, filler, organic or inorganic fine particles, antifungal agent, and silane coupling agent can be blended. The amount of these additives is suitably determined in accordance with its purpose and application.

When the polyurethane coating agent is produced by using a biomass material (biomass material-derived pentamethylenediisocyanate, etc.), the biobased content is, for example, 10% or more, preferably 25% or more, more preferably 50% or more, further preferably 75% or more.

The polyurethane coating agent can be used for coating, for example, after mixing the main component and the curing agent, over the eyewear frame by any coating method such as spray coating, air spray coating, brush coating, dip coating, a roll coater method, and a flow coater method. The amount of coating is set suitably in accordance with the purpose and application.

The eyewear frame is composed of the above-described eyewear material containing the thermoplastic polyurethane, and therefore has excellent processability and mechanical strength, and furthermore, the above-described eyewear material has a tan δ peak by dynamic viscoelasticity measurement at less than 0° C., and therefore excellent contact can be obtained. Moreover, the above-described eyewear material has a tan δ peak by dynamic viscoelasticity measurement at 0° C. or more and 70° C. or less, and therefore excellent fit can be achieved.

The eyewear frame is lightweight, and furthermore, has excellent flexibility, and can be resilient excellently even when it undergoes stress deformation. Furthermore, as described above, by coating with, for example, a polyurethane coating agent, appearance, solvent resistance, and design can be improved.

The present invention includes an eyewear.

The eyewear includes the above-described eyewear frame and an optical lens attached to the eyewear frame.

The optical lens is not particularly limited as long as it has desired optical properties, and is formed from optical resin such as for example, including glass, for example, optical acrylic resin, optical polycarbonate resin, optical polyamide resin, optical polyurethane resin, and optical epoxy resin (including thioepoxy).

For the optical lens, preferably, optical lens composed of optical resin is used, and more preferably, optical lens composed of optical polyurethane is used.

The optical polyurethane can be produced by reaction of a polyisocyanate component with an active hydrogen group-containing component.

Examples of the polyisocyanate component used for the optical polyurethane include the above-described polyisocyanate component (polyisocyanate component used for production of eyewear material).

Furthermore, the polyisocyanate component used for optical polyurethane includes sulfur containing aliphatic polyisocyanate and sulfur containing aromatic polyisocyanate.

The sulfur containing aliphatic polyisocyanate is an aliphatic polyisocyanate containing sulfur in its molecule, and examples thereof include bis(isocyanatoethyl) sulfide, bis (isocyanatopropyl) sulfide, bis(isocyanatomethyl) sulfone, bis(isocyanatomethyl) disulfide, bis(isocyanatopropyl) disulfide, bis(isocyanatomethylthio) methane, bis(isocyanatomethylthio) ethane, bis(isocyanatoethylthio) methane, bis(isocyanatoethylthio) ethane, and 1,5-diisocyanato-2-isocyanatomethyl-3-thiapentane.

The sulfur containing aromatic polyisocyanate is an aromatic polyisocyanate containing sulfur in its molecule, and examples thereof include bis(3-isocyanatophenyl) sulfide, bis(4-isocyanatophenyl) sulfide, bis(3-isocyanatomethylphenyl) sulfide, bis(4-isocyanatomethylphenyl) sulfide, bis (3-isocyanatomethylbenzyl) sulfide, bis(4-isocyanatomethylbenzyl) sulfide, bis(3-isocyanatophenyl) disulfide, bis(4-isocyanatophenyl) disulfide, bis(3-isocyanatomethylphenyl) disulfide, and bis(4-isocyanatomethylphenyl) disulfide.

These polyisocyanate components may be used singly or in combination of two or more.

For the polyisocyanate component used for the optical polyurethane, preferably, aliphatic polyisocyanate (including alicyclic polyisocyanate) and aromatic polyisocyanate are used, preferably 1,3-xylylene diisocyanate, 2,4-tolylene diisocyanate, 2,6-tolylene diisocyanate, 4,4'-diphenylmethane diisocyanate, norbornanediisocyanate, methylenebis(cyclohexyl isocyanate), 1,3-bis(isocyanatomethyl) cyclohexane, 1,4-bis(isocyanatomethyl) cyclohexane, hexamethylenediisocyanate, isophoron diisocyanate, and/or a derivative thereof, more preferably 1,3-xylylene diisocyanate, pentamethylenediisocyanate, norbornanediisocyanate, and/or a derivative thereof, even more preferably, pentamethylenediisocyanate and/or a derivative thereof is used.

Use of pentamethylenediisocyanate and/or a derivative thereof improves transparency and shock-resistant properties of optical polyurethane.

For the active hydrogen group-containing component used for the optical polyurethane, for example, the above-described active hydrogen group-containing component (active hydrogen group-containing component used for production of eyewear material) can be used, and to be more specific, the above-described polyol component, and the above-described polyamine component can be used.

For the active hydrogen group-containing component used for the optical polyurethane, a polythiol component can be used.

The polythiol component is a compound having two or more thiol groups (mercapto group) as active hydrogen groups, and for example, an aliphatic thiol compound, an aliphatic thiol compound including ester linkage, and an aromatic thiol compound can be used.

Examples of the aliphatic thiol compound include methanedithiol, 1,2-ethanedithiol, 1,2-propane dithiol, 1,3-propane dithiol, 1,4-butanedithiol, 1,5-pentanedithiol, 1,6-hexanedithiol, 1,2-cyclohexanedithiol, 3,4-dimethoxybutane-1,2-dithiol, 2-methylcyclohexane-2,3-dithiol, 1,2-dimercaptopropylmethylether, 2,3-dimercaptopropylmethylether, bis(2-mercaptoethyl) ether, tetrakis (mercaptomethyl) methane, bis(mercaptomethyl) sulfide, bis(mercaptomethyl) disulfide, bis(mercaptoethyl) sulfide, bis(mercaptoethyl) disulfide, bis(mercaptomethylthio) methane, bis(2-mercaptoethylthio) methane, 1,2-bis (mercaptomethylthio) ethane, 1,2-bis(2-mercaptoethylthio) ethane, 1,3-bis(mercaptomethylthio) propane, 1,3-bis(2-mercaptoethylthio) propane, 1,2,3-tris (mercaptomethylthio) propane, 1,2,3-tris (2-mercaptoethylthio) propane, 1,2, 3-tris (3-mercaptopropylthio) propane, 4-mercaptomethyl-1,8-dimercapto-3,6-dithiaoctane, 5,7-dimercaptomethyl-1, 11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 1,1,3,3-tetrakis (mercaptomethylthio) propane, 2,5-dimercaptomethyl-1,4-dithiane, 4,6-bis(mercaptomethylthio)-1,3-dithiane, 2-(2,2-bis(mercaptomethylthio) ethyl)-1, 3-dithietane, tetrakis (mercaptomethylthiomethyl) methane, tetrakis (2-mercaptoethylthiomethyl) methane, bis(2,3-dimercaptopropyl) sulfide, and 2,5-dimercapto-1,4-dithiane.

Examples of the aliphatic thiol compound including ester linkage include ethylene glycolbis(2-mercaptoacetate), ethylene glycolbis(3-mercaptopropionate), diethylene glycol (2-mercaptoacetate), diethylene glycol (3-mercaptopropionate), 2,3-dimercapto-1-propanol (3-mercaptopropionate), 3-mercapto-1,2-propanediolbis(2-mercaptoacetate), 3-mercapto-1,2-propanedioldi (3-mercaptopropionate), trimethylolpropanetris (2-mercaptoacetate), trimethylolpropane (3-mercaptopropionate), trimethylolethanetris (2-mercaptoacetate), trimethylolethanetris (3-mercaptopropionate), pentaerythritoltetrakis (2-mercaptoacetate), pentaerythritoltetrakis (3-mercaptopropionate), glycerintris (2-mercaptoacetate), glycerintris (3-mercaptopropionate), 1,4-cyclohexanediolbis(2-mercaptoacetate), 1,4-cyclohexanediolbis (3-mercaptopropionate), hydroxymethylsulfidebis (2-mercaptoacetate), hydroxymethylsulfidebis (3-mercaptopropionate), hydroxyethyl sulfide (2-mercaptoacetate), hydroxyethyl sulfide (3-mercaptopropionate), hydroxymethyldisulfide (2-mercaptoacetate), hydroxymethyldisulfide (3-mercaptopropionate), thioglycolic acid bis(2-mercaptoethylester), and thiodipropionic acid bis(2-mercaptoethylester).

Examples of the aromatic thiol compound include 1,2-dimercaptobenzene, 1,3-dimercaptobenzene, 1,4-dimercaptobenzene, 1,2-bis(mercaptomethyl) benzene, 1,4-bis(mercaptomethyl) benzene, 1,2-bis(mercaptoethyl) benzene, 1,4-bis(mercaptoethyl) benzene, 1,2,3-trimercaptobenzene, 1,2,4-trimercaptobenzene, 1,3,5-trimercaptobenzene, 1,2,3-tris (mercaptomethyl) benzene, 1,2,4-tris (mercaptomethyl) benzene, 1,3,5-tris (mercaptomethyl) benzene, 1,2,3-tris (mercaptoethyl) benzene, 1,3,5-tris (mercaptoethyl) benzene, 1,2,4-tris (mercaptoethyl) benzene, 2,5-toluenedithiol, 3,4-toluenedithiol, 1,4-naphthalenedithiol, 1,5-naphthalenedithiol, 2,6-naphthalenedithiol, 2,7-naphthalenedithiol, 1,2,3,4-tetramercaptobenzene, 1,2,3,5-tetramercaptobenzene, 1,2,4,5-tetramercaptobenzene, 1,2,3,4-tetrakis (mercaptomethyl) benzene, 1,2,3,5-tetrakis (mercaptomethyl) benzene, 1,2,4,5-tetrakis (mercaptomethyl) benzene, 1,2,3,4-tetrakis (mercaptoethyl) benzene, 1,2,3,5-tetrakis (mercaptoethyl) benzene, 1,2,4,5-tetrakis (mercaptoethyl) benzene, 2,2'-dimercaptobiphenyl, and 4,4'-dimercaptobiphenyl.

These polythiol components may be used singly or in combination of two or more.

These active hydrogen compound components may be used singly or in combination of two or more.

For the active hydrogen group-containing component used for the optical polyurethane, preferably, polyol component, polythiol component, more preferably, polythiol component is used. Examples of the polythiol component include, preferably, aliphatic thiol compound and aliphatic thiol compound including ester linkage, further preferably 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, ethylene glycolbis(3-mercaptopropionate), pentaerythritoltetrakis (2-mercaptoacetate), pentaerythritoltetrakis (3-mercaptopropionate), 1,1,3,3-tetrakis (mercaptomethylthio) propane, 2,5-dimercaptomethyl-1,4-dithiane, 4,6-bis(mercaptomethylthio)-1,3-dithiane, 2-(2,2-bis(mercaptomethylthio) ethyl)-1,3-dithietane, and particularly preferably 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, and pentaerythritoltetrakis (3-mercaptopropionate).

The optical lens is preferably produced from a biomass material. To be more specific, preferably, optical polyurethane is produced from reaction of a biomass material-derived polyisocyanate component and a biomass material-derived active hydrogen group-containing component, and optical lens is produced by using the optical polyurethane.

Examples of the biomass material-derived polyisocyanate component include a plant derived polyisocyanate produced by using a plant derived amino acid material as a material, and converting the amino group into the isocyanate group.

To be more specific, for example, a biomass material-derived pentamethylenediisocyanate produced by the method described in Examples in WO2011/108473 can be used: decarboxylation reaction of a lysine material, a biomass material, is performed and amino group is converted to isocyanate group.

The biomass material-derived polyisocyanate component is not limited to the above-described examples, and various biomass material-derived polyisocyanate components may be used. To be more specific, for example, a plant derived aliphatic polyisocyanate produced by the following can be used: acid amide is formed and reduced from a bivalent carboxylic acid of a plant derived material to convert into terminal amino group, and further reaction with phosgene is performed and the amino group is converted to the isocyanate group.

For the biomass material-derived active hydrogen group-containing component, for example, a biomass material-derived polythiol component (preferably, aliphatic thiol compound) is used.

Examples of the biomass material-derived polythiol component include 4-mercaptomethyl-1,8-dimercapto-3,6-dithiaoctane, 4,8 or 4,7 or 5,7-dimercaptomethyl-1,11-dimercapto-3,6,9-trithiaundecane synthesized by using epichlorohydrin produced by chlorination and epoxidation of glycerin produced from a plant derived material as a material.

To be more specific, for example, 2-mercaptoethanol is added to the above-described epichlorohydrin produced from glycerin, and the product is allowed to react with a sulfuration agent such as thiourea, and the product is decomposed with a base. In this manner, a plant derived 4-mercaptomethyl-1,8-dimercapto-3,6-dithiaoctane, a plant derived 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane can be synthesized.

Glycerin can be produced from fatty ester of glycerin contained in vegetable oils of, for example, colza oil, palm oil, castor oil, and olive oil by hydrolysis or transesterification treatment.

For the biomass material-derived active hydrogen group-containing component, in addition to the above-described biomass material-derived polythiol component, biomass material-derived polyol components such as, for example, a plant derived polytetramethylene ether polyol and a plant derived polyesterpolyol can be used.

The biomass material-derived active hydrogen group-containing component is not limited to the above-described examples, and various biomass material-derived active hydrogen group-containing components may be used.

By producing an optical polyurethane from a biomass material using these biomass material-derived polyisocyanate component and the biomass material-derived active hydrogen group-containing component, the optical lens composed of the optical polyurethane can substantially reduce the carbon dioxide emission amount at the time of combustion, and reduce burden on earth environment.

When the optical polyurethane is produced by using the biomass material, the biobased content is, for example, 5% or more, preferably 25% or more, more preferably 40% or more, and further preferably 60% or more.

The biobased content can be determined in conformity with Examples to be described later.

The optical polyurethane can be produced by allowing the above-described polyisocyanate component to react with the above-described active hydrogen group-containing component.

The polyisocyanate component is mixed with the active hydrogen group-containing component at a ratio such that the equivalent ratio (active hydrogen group/NCO) of the active hydrogen group (hydroxyl group, amino group, mercapto group) in the active hydrogen group-containing component relative to the isocyanate group (NCO) in the polyisocyanate component is, for example, 0.8 or more, preferably 0.85 or more, more preferably 0.9 or more, and for example, 1.2 or less, preferably 1.15 or less, more preferably 1.1 or less. When the equivalent ratio is in the above-described range, an optical material, in particular an optical polyurethane suitable as an eyewear plastic lens material can be produced.

The polymerization method is not particularly limited, but preferably, cast polymerization is used.

In this method, first, a mixture of the polyisocyanate component and the active hydrogen group-containing component is injected in a mold having a lens shape and held by, for example, a gasket and a tape, and as necessary, treatments such as degassing under reduced pressure and filtering (pressurized filter, depressurized filter) are conducted, and thereafter, the polyisocyanate component and the active hydrogen group-containing component are polymerized.

In this polymerization, as necessary, a reaction catalyst can be blended.

The reaction catalyst is not particularly limited, and a known reaction catalyst used in production of polythiourethane resin, and the above-described known urethanizing catalyst are used.

The mixing ratio of the reaction catalyst is set suitably in accordance with the purpose and application.

The reaction conditions are suitably set in accordance with the types and the amount of the material component and the catalyst, and the mold shape, but for example, the reaction temperature is −50 to 150° C., and the reaction time is 1 to 50 hours. Depending on the cases, the temperature is kept or increased gradually in a temperature range of 10 to 150° C., and curing is performed for 1 to 25 hours.

The optical polyurethane is annealed as necessary. The annealing temperature is, for example, 50° C. or more, preferably 90° C. or more, more preferably 100° C. or more, and for example, 150° C. or less, preferably 140° C. or less, more preferably 130° C. or less.

When producing an optical polyurethane, as necessary, known additives, for example, internal mold release agents, resin modifiers, and chain extenders, cross-linking agents, light stabilizers, ultraviolet ray absorbents, antioxidants, color protection agents, solvent dyes, fillers, and adhesion improvement agents can further be added at a suitable ratio.

Examples of the internal mold release agent include acid phosphate, to be more specific, for example, phosphoric acid monoester and phosphoric acid diester.

These internal mold release agents may be used singly or in combination of two or more.

The mixing ratio of the internal mold release agent is set suitably in accordance with the purpose and application.

The resin modifier is blended to adjust optical properties and mechanical characteristics of the optical polyurethane, and furthermore for improvement in handleability of the material component (monomer).

For the resin modifier, to be specific, for example, olefin compounds such as an episulfide compound, alcohol compound, amine compound, epoxy compound, organic acid and its anhydride, and (meth)acrylate compound are used.

These resin modifiers may be used singly or in combination of two or more.

The mixing ratio of the resin modifier is set suitably in accordance with the purpose and application.

In the production of the optical polyurethane, these additives (internal mold release agent, resin modifier, etc.) can be added at the time of synthesizing the material components; can be blended in advance to the synthesized material component; can be blended at the time of blending the material components; and furthermore, can also be added after mixing. Preferably, the additives can be added at the time of mixing of the material components.

Then, such a reaction allows production of an optical polyurethane having a desired shape (e.g., lens shape), and the produced optical polyurethane can be used as an optical lens.

The optical lens (plastic lens) produced by using the optical polyurethane can have a coating layer, as necessary, laminated on one side or both sides.

For the coating layer, for example, primer layers, hard coat layers, antireflection coating layers, antifogging coating layers, soil resistance layers, and water-repellent layers are used.

These examples of the coating layer can be laminated on the optical lens as a single layer, or can be laminated on the optical lens as multiple layers.

When the coating layer is to be made into multiple layers, or when the coating layer is laminated on both sides of the optical lens, the coating layer can be the same or different.

Such an optical lens is preferably attached (fit) to the above-described eyewear frame, and an eyewear is formed.

The biobased content of the eyewear as a whole (eyewear frame, optical lens, and coating agent) is, for example, 10% or more, preferably 25% or more, more preferably 50% or more, further preferably 75% or more.

The produced eyewear contains the above-described thermoplastic polyurethane in the eyewear frame, and therefore has excellent processability and mechanical strength, and furthermore, the produced eyewear has a tan δ peak in less than 0° C. by dynamic viscoelasticity measurement, and therefore excellent contact can be produced, and moreover has a tan δ peak in 0° C. or more and 70° C. or less by dynamic viscoelasticity measurement, and therefore has excellent fit.

Therefore, the above-described eyewear is suitably used in eyewears such as corrective glasses, protection glasses, sunglasses, and goggles, to be more specific, eyewear for sports; eyewear having antifogging functions and used in places with high temperature and high humidity such as bathroom and sauna; eyewear with electronic devices having functions to receive distributed music and images; eyewear having electronic lens having liquid crystal functions; and furthermore, eyewear for internet functions, eyewear for pollen prevention, eyewear for vision care for short sight, long sight, and presbyopia, eyewear for cataract and glaucoma prevention, and eyewear having spiritually relaxing aroma.

EXAMPLES

In the following, the present invention will be described based on Examples and Comparative Examples, but the present invention is not limited thereto.

In the following description, the units "part(s)" and "%" are by mass, unless otherwise noted. The values shown below in Examples can be replaced with corresponding values (that is, upper limit value or lower limit value) shown in embodiments.

Synthesis Example 1 (Synthesis of 1,4-BIC)

A stainless steel reactor equipped with a stirrer, a thermometer, a nitrogen inlet tube, a chlorine gas inlet tube, a phosgene inlet tube, a gas discharge pipe, a gas cooling device, and an automatic pressure adjustment valve was charged with 55 parts by mass of 1,4-bis(aminomethyl) cyclohexane (trans/cis ratio of 84/16 determined based on $^{13}$C-NMR manufactured by MITSUBISHI GAS CHEMICAL COMPANY, INC.) and 700 parts by mass of orthodichlorobenzene, and the mixture was heated to 60° C. while stirring at 300 rpm. Thereafter, hydrochloric acid gas was introduced at a flow rate of 1.0 mol/hr (relative to 1,4-BAC) in an amount 3.0 mol times relative to 1,4-BAC. Cold water was allowed to pass through the reactor jacket, thereby keeping the internal temperature to 60 to 100° C.

Next, 77 parts by mass of phosgene was added thereto, and while increasing the temperature of the reaction solution to 150° C., the pressure was increased to 0.2 MPa (gauge pressure), and furthermore, reaction was performed under a pressure of 0.2 MPa (gauge pressure) and a reaction temperature of 150° C. while adding phosgene for 6 hours. The phosgene added during the reaction was 230 parts by mass.

After the termination of reaction, nitrogen gas was allowed to pass through at 100 to 150° C. to degas. Then, after distilling off the solvent orthodichlorobenzene under reduced pressure, 1,4-bis(isocyanatomethyl) cyclohexane was distilled off also under reduced pressure.

Then, the distilled 1,4-bis(isocyanatomethyl) cyclohexane was introduced into a reactor equipped with a stirrer, a thermometer, a reflux pipe, and a nitrogen inlet tube, and heated while introducing nitrogen under normal pressure at 190° C. for 4 hours.

Then, a flask equipped with a packed column (filler: Heli pack, theoretical plate number: 10) was charged with the 1,4-bis(isocyanatomethyl) cyclohexane after heat treatment and rectification was performed.

The rectification conditions are as follows: column top pressure 0.3 to 1.3 kPa, reflux ratio 1, column top temperature 120 to 145° C., column bottom temperature (vessel temperature) 160 to 170° C., and column bottom residence time 4 hours. The fraction of the distillation rate of 10 mass % to 95 mass % relative to the charged mass was recovered, thereby producing 1,4-BIC.

Based on the gas chromatography measurement, the produced 1,4-BIC has a purity of 99.8% and a trans isomer ratio of 85 mol %.

Synthesis Example 2 (Synthesis of Prepolymer (a))

A four-neck flask equipped with a stirrer, a thermometer, a reflux pipe, and a nitrogen inlet tube was charged with 24.1 parts by mass of PTG2000SN (P)(manufactured by Hodogaya Chemical Co., LTD., polytetramethylene ether glycol in which biomass material is used, number average molecular weight 2000) and 23.6 parts by mass of PTG1000SN (P)(manufactured by Hodogaya Chemical Co., LTD., polytetramethylene ether glycol in which biomass material is used, number average molecular weight 1000), and then 38.0 parts by mass of 1,4-BIC was introduced so that the equivalent ratio (NCO/OH) was 5.46. After stirring at 80° C. for 1 hour in a nitrogen atmosphere, 0.011 parts by mass of Stanoct (stannous octoate manufactured by API CORPORATION) diluted with DINA (diisononyladipate manufactured by J-PLUS Co., Ltd.) to 4 mass % was introduced. Furthermore, reaction was performed until the isocyanate group content was 15.67 mass %, thereby producing isocyanate group-terminated prepolymer (hereinafter may be referred to as prepolymer)(a).

Synthesis Examples 3 to 13 (Synthesis of Prepolymers (b) to (l))

Isocyanate group-terminated prepolymers (b) to (1) were produced in the same manner as in Synthesis Example 2 based on the blending ratios shown in Tables 1 to 4.

Example 1 (Preparation of Eyewear Material (A) and Eyewear Frame (A))

A stainless steel vessel was charged with 85.71 parts by mass of prepolymer (a) adjusted in advance to 80° C., 0.3 parts by mass of IRGANOX 245 (Heat-resistant stabilizer manufactured by BASF Japan), 0.1 parts by mass of TINUVIN 234 (Ultraviolet ray absorbent manufactured by BASF Japan), 0.1 parts by mass of ADK STAB LA-72 (Light stabilizer manufactured by ADEKA), and 0.013 parts by mass of a catalyst liquid in which Stanoct (Stannous octoate manufactured by API Corporation) was diluted with DINA (diisononyladipate manufactured by J-PLUS Co., Ltd.) to 4 mass %, and the mixture was stirred and mixed at 800 rpm for about 2 minutes using a high-speed disper. Then, 1,4-butanediol (manufactured by Wako Pure Chemical Industries, Ltd., in the following abbreviated as 1,4-BD) was adjusted to 80° C., and added so that the equivalent ratio (NCO/OH) was 1.01.

Thereafter, sufficient stirring was conducted until the entire mixture was homogenous for about 10 minutes, and homogeneity of the reaction mixture liquid was checked right after the termination of stirring. Thereafter, the reaction mixture liquid was introduced into an SUS (stainless steel) vat having a temperature adjusted in advance to 150° C., and reaction was performed at 150° C. for 1 hour, and then performed at 100° C. for 23 hours, thereby producing thermoplastic polyurethane (A).

The thermoplastic polyurethane (A) was taken out from the vat, and aged under constant temperature and constant humidity of a room temperature of 23° C. and a relative humidity of 50% for 7 days.

The produced thermoplastic polyurethane (A) was named eyewear material (A).

Thereafter, the eyewear material (A) was cut into dices with a bale cutter, and the diced resin was ground with a grinder. The ground pellet was dried under nitrogen flow at 80° C. for a whole day. Strands were extruded using a uniaxial extruder (model: SZW40-28MG, manufactured by TECHNOVEL) at a cylinder temperature range of 185 to 245° C., and they were cut, thereby producing pellets of eyewear material (A). The produced pellets were further dried for a whole day under a nitrogen flow at 80° C.

Then, using an injection molding machine (model: NEX-140, manufactured by NISSEI PLASTIC INDUSTRIAL CO., LTD.), injection molding was performed at settings of a screw number of revolution of 80 rpm and a barrel temperature of 210 to 235° C., and conditions of a mold temperature of 30° C., an injection time of 10 seconds, an injection speed of 60 mm/s, and a cooling time of 45 seconds, thereby producing eyewear frame (A).

The eyewear frame (A) is a full rim type eyeglass frame including parts such as a hinge (connecting portion between end piece and temple) and an eyewear frame including nose pads, earpiece (ear pads), temple (string portion), rim (lens surrounding), bridge (rim connecting portion), and end piece (front both end portions).

In the following, all of the produced eyewear frames have the same shape.

A sheet having a 2 mm thickness for physical properties measurement was produced under the same conditions. The produced sheet having a 2 mm thickness was aged at constant temperature and humidity conditions of a room temperature of 23° C. and a relative humidity of 55% for 7 days, and thereafter physical properties were measured.

Example 2 (Preparation of Eyewear Material (B) and Eyewear Frame (B))

A stainless steel vessel was charged with 85.71 parts by mass of prepolymer (a) adjusted in advance to 80° C., 0.0007 parts by mass of CHALINE® R-170S (manufactured by Nissin Chemical Industry Co., Ltd., acryl-modified polyorganosiloxane), 0.3 parts by mass of IRGANOX 245 (Heat-resistant stabilizer manufactured by BASF Japan), 0.1 parts by mass of TINUVIN 234 (Ultraviolet ray absorbent manufactured by BASF Japan), 0.1 parts by mass of ADK STAB LA-72 (Light stabilizer manufactured by ADEKA), and 0.013 parts by mass of a catalyst liquid in which Stanoct (Stannous octoate manufactured by API Corporation) was diluted in DINA (diisononyladipate manufactured by J-PLUS Co., Ltd.) to 4 mass %, and the mixture was stirred at 800 rpm for about 2 minutes using a high-speed disper. Then, 1,4-butanediol (manufactured by Wako Pure Chemical Industries, Ltd., in the following abbreviated as 1,4-BD) was adjusted to 80° C., and added so that the equivalent ratio (NCO/OH) was 1.01.

Thereafter, sufficient stirring was conducted until the entire mixture was homogenous about for 10 minutes, and homogeneity of the reaction mixture liquid was checked right after the termination of stirring. Thereafter, the reaction mixture liquid was introduced into an SUS vat having a temperature adjusted in advance to 150° C., and reaction was performed at 150° C. for 1 hour, and then performed at 100° C. for 23 hours, thereby producing thermoplastic polyurethane (B) containing acryl-modified polyorganosiloxane.

The thermoplastic polyurethane (B) was taken out from the vat, and aged under constant temperature and constant humidity of a room temperature of 23° C. and a relative humidity of 50% for 7 days.

The produced thermoplastic polyurethane (B) was named eyewear material (B).

Thereafter, the eyewear material (B) was treated in the same manner as in Example 1, thereby producing eyewear frame (B) and a sheet having a thickness of 2 mm.

Examples 3 to 18, Comparative Examples 1 to 2 (Preparation of Thermoplastic Polyurethanes C to T and Eyewear Frames C to T)

Thermoplastic polyurethanes C to U and eyewear materials C to U, and eyewear frames C to U were prepared in the same manner as in Example 1 or Example 2, except that the mixing formulation was changed as shown in Tables 1 to 4.

Comparative Example 3 (Preparation of Thermoplastic Polyurethane U and Eyewear Frame U)

A stainless steel vessel was charged with 25.6 parts by mass of 1,4-BIC, 25.6 parts by mass of 1,3-BIC, 5.7 parts by mass of PTG650 (manufactured by Hodogaya Chemical Co., LTD. polytetramethylene ether glycol), 0.05 parts by mass of CHALINE® R-170S, 0.3 parts by mass of IRGANOX 245 (Heat-resistant stabilizer manufactured by BASF Japan), 0.1 parts by mass of TINUVIN 234 (Ultraviolet ray absorbent manufactured by BASF Japan), 0.1 parts by mass of ADK STABLA-72 (Light stabilizer manufactured by ADEKA), 13.0 parts by mass of 1,6-hexanediol (manufactured by Wako Pure Chemical Industries, Ltd. 1,6-HDO), 23.8 parts by mass of cyclohexanedimethanol (manufactured by Wako Pure Chemical Industries, Ltd. CHDM cis, trans mixture), and 0.013 parts by mass of a catalyst liquid in which Stanoct (Stannous octoate manufactured by API Corporation) was diluted in DINA (diisononyladipate manufactured by J-PLUS Co., Ltd.) to 4 mass %, and the mixture was stirred at 800 rpm for about 10 minutes using a high-speed disper until the entire mixture was homogenous. Thereafter, homogeneity of the reaction mixture liquid was checked right after the termination of stirring. Thereafter, the reaction mixture liquid was introduced into an SUS vat having a temperature adjusted in advance to 150° C., and reaction was performed at 150° C. for 1 hour, and then performed at 100° C. for 23 hours, thereby producing thermoplastic polyurethane (U).

The produced thermoplastic polyurethane (U) was treated in the same manner as in Example 1, thereby producing eyewear frame (U) and a sheet having a 2 mm thickness.

Evaluation

The following Evaluations were conducted for the eyewear frame and sheet produced in Examples and Comparative Examples.

The results are shown in Tables 1 to 4.

<Hardness: Shore D>

Shore D hardness of the thermoplastic polyurethane was measured in conformity with the hardness test of JIS K7311 (1995), and the results are shown as numeral values.

<Specific Gravity>

The specific gravity of the eyewear material was measured in conformity with JIS Z8807 (2012).

<Biobased Content>

The biobased content was measured in conformity with the standard of ASTM D6866 METHOD-B.

To be specific, after the sample was combusted and $CO_2$ was purified, graphite was prepared and $^{14}C$ concentration was measured with AMS (accelerator mass spectroscopy), thereby calculating the biobased content.

<Hard Segment Concentration>

The hard segment concentration was calculated from the mixing formulation (charged) of the components based on the following formula.

[chain extender (g)+(chain extender (g)/molecular weight of chain extender (g/mol))×average molecular weight of polyisocyanate component (g/mol)]÷(polyisocyanate component (g)+active hydrogen group-containing component (g))×100

The hard segment concentration was measured also based on the following method for only Example 1.

That is, in accordance with the measurement method described in Satoshi Yamasaki et. al "Effect of aggregation structure on rheological properties of thermoplastic polyurethanes" (Polymer, vol. 48, 4793 to 4803 pages, 2007) mentioned above, Free Induction Decay (FID) signal was determined at a measurement temperature of 30° C. of 1H nuclei using a solid-state NMR device (manufactured by JEOL Ltd., model: JNM-MU25) with a solid echo method.

The obtained FID signal was separated into components based on approximation by the method of least squares, using formula 1) of magnetization intensity composed of Gaussian-type for the component having short relaxation time and Lorentz type for components having medium and longest relaxation time.

M ($t_f$) is a standardized initial value of magnetization intensity of a component with a short relaxation time, M ($t_s$) is a standardized initial value of magnetization intensity of a component with a long relaxation time, and M ($t_i$) is a standardized initial value of magnetization intensity of a component with a medium relaxation time.

$T_{2f}$, $T_{2s}$ and $T_{2i}$ are spin-spin relaxation time of corresponding component. The initial values (M (tf), M (ts), and M (ti)) of the components with short, long, and medium relaxation time, of standardized magnetization intensity were assigned to hard segment phase, soft segment phase, and their interface phase, respectively, and the hard segment concentration was calculated based on their relative proton content. Measurement conditions are as follows: $^1$H nuclei 25 MHz, 90° pulse width 2.0 μs, repetition time 4 s, and scanning time 16. Using this method, the hard segment concentration of thermoplastic polyurethane A described in Example 1 was determined to be 43%.

$$M(t)=M(t_f)\exp(-t^2/T_{2f}^2)+M(ti)\exp(-t/T_{2i})+M(t_s)\exp(-t/T_{2s}) \quad \text{Formula 1})$$

<Tensile Strength and Elongation at Break (Unit: Mpa and %)>

In accordance with "JIS K7312 Physical testing methods for molded products of thermosetting polyurethane elastomers", tensile test using the thermoplastic urethane sheet was performed. Test piece was punched with a JIS-3 dumb-bell, and using Tensilon (manufactured by A&D Company, Limited, model: RTG-1310), the measurement was conducted with conditions of a gauge length of 20 mm and a tensile speed of 500 mm/min.

<Glass Transition Temperature Tg (Unit: ° C.)>

The test sample of the thermoplastic polyurethane sheets (2 mm thickness) was punched with a dumbbell into a size of a width of 5 mm and a length of 50 mm.

Then, to the sample, using a dynamic viscoelasticity measuring apparatus (manufactured by IT Engineering, model: DVA-200), the dynamic viscoelasticity of the test sample was measured under the conditions of the following: tensile mode, gauge length 25 mm, temperature increase rate 5° C./min, and measurement frequency 10 Hz at −100 to 250° C. The tan δ peak temperature was calculated as Tg, and the results are shown as numeral values.

<Comfortability (Fit and Contact)>

Fit and surface contact when the eyewear frame is worn were evaluated.

Criteria for Evaluation are shown below.

Fit Evaluation
5: No slippage when walking.
4: Slight slippage when walking.
3: Slippage when walking.
2: Great Slippage when walking.
1: Not wearable.

Surface Contact Evaluation
5: No sticking to the skin.
4: Slight sticking to the skin.
3: Sticking to the skin.
2: Great sticking to the skin.
1: Great sticking and discomfort.

<Bending Resistance>

After bending the string portion of the eyewear frame to 90°, the degree of resilience was visually evaluated.
Evaluation criteria are shown below.

5: No deformation.
4: Slightly deformed.
3: Deformed.
2: Deformed and cracked.
1: Caused breakage.

<Stain Resistance>

The frame was immersed in Sun oil (Hawaiian tropic royal oil, manufactured by royal oil) at 40° C. for 24 hours. Thereafter, the frame was washed with tap water, and appearance was observed visually.
Criteria for Evaluation are shown below.
5: No change.
4: Slight whitening was confirmed.
3: Whitening was confirmed.
2: Whitening and swelling were confirmed.
1: Swelling was confirmed.

<Preparation of Optical Lens and Eyewear>

Production Example 1 (Production of 1,5-pentamethylenediisocyanate)

A pressurized reactor with jacket equipped with an electromagnetic induction stirrer, an automatic pressure regulating valve, a thermometer, a nitrogen inlet line, a phosgene inlet line, a condenser, and a material feed pump was charged with 2000 parts by mass of o-dichlorobenzene. Then, 2300 parts by mass of phosgene was added from the phosgene inlet line, and stirring was started. Cold water was allowed to go through the reactor jacket so that the internal temperature was kept to about 10° C.

To the reactor, a solution in which 400 parts by mass of 1,5-pentamethylenediamine prepared by the method described in Example 12 of WO2011/108473 was dissolved in 2600 parts by mass of o-dichlorobenzene was fed, taking 60 minutes using a feed pump, and cold phosgenation was started at 30° C. or less under normal pressure. After the completion of the feed, a light-brown white slurry was formed in the pressurized reactor.

Then, while the temperature of the internal liquid of the reactor was gradually increased to 160° C., the pressure was increased to 0.25 MPa, and further hot phosgenation was performed under a pressure of 0.25 MPa, and at a reaction temperature of 160° C. for 90 minutes. During the hot phosgenation, 1100 parts by mass of phosgene was further added. In the process of the hot phosgenation, the internal liquid of the pressurized reactor became light-brown clear solution. After completion of hot phosgenation, at 100 to 140° C., nitrogen gas was allowed to pass through at 100 L/hour, and degassing was performed.

Thereafter, o-dichlorobenzene was distilled off under reduced pressure, and then 1,5-pentamethylenediisocyanate was distilled off also under reduced pressure, thereby producing 558 parts by mass of 1,5-pentamethylenediisocyanate having a purity of 98.7%.

Then, 558 parts by mass of 1,5-pentamethylenediisocyanate, and 0.02 parts by mass of tris (tridecyl) phosphate (manufactured by Johoku Chemical Co. Ltd., trade name: JP-333E) relative to 100 parts by mass of 1,5-pentamethylenediisocyanate was introduced into a four-neck flask equipped with a stirrer, a thermometer, a reflux pipe, and a nitrogen inlet tube, and while introducing nitrogen, heating at 210° C. was conducted for 2 hours under normal pressure, thereby producing 553 parts by mass of 1,5-pentamethylenediisocyanate having a purity of 98.3%. The 1,5-pentamethylenediisocyanate yield in the heat treatment was 99.6%.

Then, the 1,5-pentamethylenediisocyanate after the heat treatment was introduced into a glass flask. Further rectification was conducted with refluxing under conditions of 127 to 132° C. and 2.7 KPa, using a rectification apparatus equipped with a cooler and a distillation column (manufactured by SIBATA SCIENTIFIC TECHNOLOGY LTD., trade name: distillation column K type) having a distillation pipe with packings (manufactured by Sumitomo Heavy Industries, Ltd., trade name: Sumitomo/Sulzer Laboratory Packings EX type) of four elements, and a reflux ratio adjusting timer, thereby producing 1,5-pentamethylenediisocyanate having a purity of 99.9 wt %. The biobased content was determined based on the method below, and the 1,5-pentamethylenediisocyanate had a biobased content of 71%.

<Biobased Content Measurement Method>

The biobased content was measured in conformity with the standard of ASTM D6866 METHOD-B.

To be specific, 1,5-pentamethylenediisocyanate was formed into methylcarbamate (urethanization) with methanol, and the biobased content of the methylcarbamate was measured. The result showed the biobased content of 56%. Based on this value, the biobased content of the 1,5-pentamethylenediisocyanate was determined based on the following formula.

Plant derived carbon number/(plant derived carbon number+petroleum based carbon number)×100

Production Example 2 (Synthesis of Polyisocyanate Composition A)

A four-necked flask equipped with a stirrer, a thermometer, a reflux pipe, and a nitrogen inlet tube was charged with 500 parts by mass of 1,5-pentamethylenediisocyanate produced in Production Example 1, 1 part by mass of isobutylalcohol, 0.3 parts by mass of 2,6-di (tert-butyl)-4-methylphenol, and 0.3 parts by mass of tris (tridecyl) phosphite, and the mixture was allowed to react at 80° C. for 2 hours.

Then, 0.05 parts by mass of N-(2-hydroxypropyl)-N,N,N-trimethylammonium-2-ethylhexanoate (manufactured by Air Products and Chemicals, Inc., trade name: DABCO (r) TMR) was added thereto as a trimer catalyst. After allowing the mixture to react for 50 minutes, 0.12 parts of o-toluenesulfoneamide was added. The produced reaction solution was allowed to pass through a thin-film distillation device, and distillated at a degree of vacuum of 0.09 KPa and a temperature of 150° C., thereby obtaining 401 parts by mass of unreacted pentamethylenediisocyanate. Furthermore, 0.02 parts by mass of o-toluenesulfoneamide was added relative to 100 parts by mass of the produced composition, thereby producing 100 parts by mass of polyisocyanate composition A.

The amount of 1,5-pentamethylenediisocyanate composing polyisocyanate composition A was 98 mass %.

The polyisocyanate composition A had an unreacted 1,5-pentamethylenediisocyanate concentration of less than 1 mass %, an isocyanurate mononuclide concentration of 65 mass %, an isocyanate group concentration of 25%, an average functionality of 3.3, and a biobased content (in conformity with the standard of ASTM D6866 METHOD-B) of 70%.

Production Example 3 (Synthesis of Biomass Material-Derived Polythiol (Polythiol Mainly Composed of 4,8, 4,7 and 5,7-Dimercaptomethyl-1,11-Dimercapto-3,6,9-Trithiaundecane))

A reactor was charged with 51.2 parts by mass of 2-mercaptoethanol, 26.5 parts by mass of degassed water (dissolved oxygen concentration 2 ppm), and 0.16 parts by mass of a 49 mass % aqueous sodium hydroxide solution.

Then, 61.99 parts by mass of plant derived epichlorohydrin (manufactured by Solvay Japan, Ltd., EPICHLOROHYDRIN (ECH)) was dropped in the reactor at 9 to 11° C. taking 6.5 hours, and stirring was continued for 60 minutes.

Then, 150.0 parts by mass of 17.3 mass % aqueous sodium sulfide solution was dropped in at 7 to 37° C. taking 5.5 hours, and stirring was conducted for 120 minutes. Then, 279.0 parts by mass of 35.5 mass % hydrochloric acid was introduced thereto.

Then, 125.8 parts by mass of thiourea having a purity of 99.9 mass % was introduced thereto, and the mixture was stirred at 110° C. while refluxing for 3 hours, performing thiuronium chloridatiion reaction. After cooling to 45° C., 214.0 parts by mass of toluene was added, the mixture was cooled to 25° C., and 206.2 parts by mass of 25 mass % ammonia aqueous solution was introduced thereto at 25 to 50° C. taking 30 minutes to allow hydrolysis reaction at 50 to 65° C. by stirring for 1 hour, thereby producing a toluene solution of polythiol.

Then, 59.4 parts by mass of 36 mass % hydrochloric acid was added to the produced toluene solution, and washed with acid at 35 to 40° C. for 30 minutes twice. Thereafter, 118.7 parts by mass of degassed water (dissolved oxygen concentration 2 ppm) was added thereto and washing was conducted at 35 to 45° C. for 30 minutes for five times.

Thereafter, toluene and a tiny amount of moisture were removed with heating under reduced pressure, and vacuum filtration was conducted with a PTFE type membrane filter of 1.2 thereby producing 115.9 parts by mass of polythiol mainly composed of 4,8-dimercaptomethyl-1,11-dimercapto-3,6,9-trithiaundecane, 4,7-dimercaptomethyl-1,11-dimercapto-3,6,9-trithiaundecane, and 5,7-dimercaptomethyl-1,11-dimercapto-3,6,9-trithiaundecane (isomer mixture of [4,8-]/[4,7-]/[5,7-]=85/5/10 (molar ratio)).

Example 19 (Optical Lens (1))

0.1 parts by mass of Zelec UN (internal mold release agent, acid phosphate: registered trademark, manufactured by Stepan Company), 0.05 parts by mass of viosorb 583 (ultraviolet ray absorbent: registered trademark, manufactured by KYODO CHEMICAL CO., LTD.), and 33.5 parts by mass of TAKENATE 500 (m-xylylene diisocyanate manufactured by Mitsui Chemicals) were mixed at room temperature for 30 minutes and dissolved. To the mixture, 56.5 parts by mass of pentaerythritoltetrakis (3-mercaptopropionate)(manufactured by SC Organic Chemical Co., Ltd.) was added, and the mixture was stirred until the mixture becomes homogenous.

Then, 0.008 parts by mass of KC-1A-1 (catalyst, manufactured by KYODO CHEMICAL CO., LTD.) was added to 10.0 parts by mass of TAKENATE 500 in a nitrogen atmosphere and the mixture was stirred and dissolved in advance in another vessel. This was added to the mixture solution as described above, and the mixture was further stirred and mixed at room temperature, thereby producing a homogenous solution of monomer mixture.

Thereafter, the produced homogenous solution was degassed at room temperature under reduced pressure for 30 minutes, filtered with a 1 µm Teflon (registered trademark) filter, and thereafter injected into a mold composed of glass mold and tape.

The mold was put into an oven, and the temperature was gradually increased from 25° C. to 120° C. taking about 24 hours, thereby performing polymerization. After the completion of polymerization, the mold was taken out from the oven, and a molded product was released from the mold, and further annealing was conducted at 120° C. for 2 hours, thereby producing a resin molded product. The resin molded product had colorless transparent appearance, and had a refraction (ne) of 1.60, an Abbe number (ve) of 36, a resin specific gravity of 1.35, a heat resistance of 92° C., and a biobased content of 0%. The evaluation methods for refraction, Abbe number, specific gravity, heat resistance, and biobased content are to be described later (the same applied to the following).

The produced resin molded product was prepared as an optical lens, and incised and polished in conformity with the eyewear frames produced in Examples 1 to 18, and attached to the eyewear frame, thereby producing an eyewear.

Example 20 (Optical Lens (2))

2.1 parts by mass of Zelec UN (internal mold release agent, acid phosphate: registered trademark, manufactured by Stepan Company), 8.0 parts by mass of ACTCOL™ HS-700A (manufactured by Mitsui Chemicals Inc., polyether polyol), and 8.0 parts by mass of glycerin (Manufactured by Wako Pure Chemical Industries, Ltd.) were mixed, and the mixture was stirred and dispersed at room temperature for 5 minutes. Thereafter, 32.0 parts by mass of polyisocyanate composition A (including isocyanurate of 1,5-pentamethylenediisocyanate) and 13.8 parts by mass of 2,5 (6)-diisocyanatomethyl[2,2,1]heptane (manufactured by Mitsui Chemicals Inc.) were added, and 1.6 parts by mass of Tinuvin292 (Ultraviolet ray absorbent manufactured by BASF Japan) was further added, and the mixture was degassed at room temperature for 30 minutes. Thereafter, the mixture was injected into a mold composed of a glass mold and a tape.

The mold was put into an oven, and the temperature was gradually increased from 30° C. to 130° C. taking about 24 hours, thereby performing polymerization. After the completion of polymerization, the mold was taken out from the oven, and a mold product was released from the mold, thereby producing a resin molded product. The produced resin molded product had colorless transparent appearance, and had a refraction (ne) of 1.52, an Abbe number (ve) of 50, a heat resistance of 111° C., a resin specific gravity of 1.23, and a biobased content of 48%.

The produced resin molded product was prepared as an optical lens, and incised and polished in conformity with the eyewear frame produced in Examples 1 to 18, and attached to the eyewear frame, thereby producing an eyewear.

Example 21 (Optical Lens (3))

0.24 parts by mass of Zelec UN (internal mold release agent, acid phosphate: registered trademark, Manufactured by Stepan Company) and 3.0 parts by mass of viosorb 583 (ultraviolet ray absorbent: registered trademark, manufactured by KYODO CHEMICAL CO., LTD.), and 48.3 parts by mass of 1,5-pentamethylenediisocyanate were mixed, and the mixture was stirred and dissolved at room temperature for 15 minutes. Thereafter, 56.3 parts by mass of polyisocyanate composition A (including isocyanurate of 1,5-pentamethylenediisocyanate) was mixed, thereby preparing a polyisocyanate solution.

Then, 66.1 parts by mass of polythiol mainly composed of 4,8, 4,7 and 5,7-dimercaptomethyl-1,11-dimercapto-3,6,9-trithiaundecane (polythiol component of Production Example 3), 29.4 parts by mass of pentaerythritoltetrakis (3-mercaptopropionate), and 0.06 parts by mass of 1-benzyl-2-methylimidazole (catalyst) were mixed, and the mixture was stirred and dissolved at room temperature for 30 minutes, thereby preparing a polythiol solution.

Then, a total amount of the above-described polyisocyanate solution and polythiol solution were mixed, and the mixture was stirred at room temperature, thereby producing a homogenous solution of monomer mixture.

Thereafter, the produced homogenous solution was degassed at room temperature under reduced pressure for 30 minutes, filtered with a 1 μm Teflon (registered trademark) filter, and then injected into a mold composed of a glass mold and a tape.

The mold was put into an oven, and the temperature was gradually increased from 25° C. to 120° C. taking about 24 hours, thereby performing polymerization. After the completion of polymerization, the mold was taken out from the oven, and a mold product was released from the mold, and further annealing was conducted at 120° C. for 2 hours, thereby producing a resin molded product. The resin molded product had colorless transparent appearance, and had a refraction (ne) of 1.60, an Abbe number (ve) of 38, a resin specific gravity of 1.29, a heat resistance of 85° C., and a biobased content of 55%.

The produced resin molded product was prepared as an optical lens, incised and polished in conformity with the eyewear frame produced in Examples 1 to 18, and attached to the eyewear frame, thereby producing an eyewear.

Evaluation

The evaluation methods for the optical lenses produced in Examples are described below.

<Optical Properties>

The refraction (ne) and the Abbe number (ve) were measured at 20° C. using Pulfrich refractometer.

<Heat Resistance>

The glass transition temperature (Tg) was measured using TMA-60 manufactured by SHIMADZU CORPORATION by TMA penetration method (50 g load, probe tip 0.5 mmϕ), and the result is regarded as heat resistance.

<Specific Gravity>

Measured at 20° C. by Archimedes method.

<Biobased Content>

The biobased content was measured in conformity with the standard of ASTM D6866 METHOD-B.

To be specific, the sample was combusted and $CO_2$ was purified, and thereafter graphite was prepared. The $^{14}C$ concentration was measured by AMS (accelerator mass spectroscopy), thereby calculating biobased content.

Example 22 (Preparation and Coating of Polyurethane Coating Agent)

1.123 parts by mass of polyisocyanate composition A including isocyanurate product of 1,5-pentamethylenediisocyanate, 13.109 parts by mass of Olester Q828 (manufactured by Mitsui Chemicals, acrylic polyol, solid content concentration 53.4 mass %, butyl acetate/methyl ethyl ketone=2/1 (parts by mass), hydroxyl value 12.5 mgKOH/g), 3.0 parts by mass of selenol H2000 (manufactured by Du Pont Kabushiki Kaisha polytrimethyleneetherglycol in which biomass material is used), and 0.0033 parts by mass of catalyst (Manufactured by Wako Pure Chemical Industries, Ltd. dibutyltin dilaurate) were mixed, and the mixture was applied onto the eyewear frame (without optical lens) and sheet produced in Examples by spray, and cured at 50° C. for 1 hour by heating.

The optical lens was attached to the coated eyewear frames in the same manner as in Examples 19 to 21, thereby producing eyewears.
Evaluation The following Evaluations were conducted for the eyewear frame and sheet produced in Example 22. The results are shown in Tables 1 to 4.
<Paintwork>

Gloss of the coating at the time of coating the thermoplastic polyurethane sheet was measured. Gloss was measured with a gloss meter (manufactured by Nippon Denshoku Industries Co., Ltd. model: Gloss Meter VG2000).
<Adherence>

Adherence between the polyurethane coating agent coating and the thermoplastic polyurethane sheet was evaluated in conformity with the standard of ASTM D3359 (2007).

In Tables, 5B indicates that the percentage where the coating was peeled was 0%, and 3B indicates 5 to 15%, and 1B indicates 35 to 65%.

TABLE 1

| | | | | | | | Ex. 1 | Ex. 2 | Ex. 3 | Ex. 4 | Ex. 5 | Ex. 6 | Ex. 7 |
|---|---|---|---|---|---|---|---|---|---|---|---|---|---|
| Eyewear material | Mixing formulation | Prepolymer | | Prepolymer type | | | a | a | a | a | a | a | a |
| | | | | Synthesis Ex. | | | 2 | 2 | 2 | 2 | 2 | 2 | 2 |
| | | | Polyisocyanate component | 1,4-BIC | | parts by mass | 38.0 | 38.0 | 38.0 | 38.0 | 38.0 | 38.0 | 38.0 |
| | | | | 1,3-BIC | | parts by mass | — | — | — | — | — | — | — |
| | | | | H12MDI | | parts by mass | — | — | — | — | — | — | — |
| | | | Active hydrogen group containing component | PTG2000SN (P) | | parts by mass | 24.1 | 24.1 | 24.1 | 24.1 | 24.1 | 24.1 | 24.1 |
| | | | | PTG1000SN (P) | | parts by mass | 23.6 | 23.6 | 23.6 | 23.6 | 23.6 | 23.6 | 23.6 |
| | | | | PTG650 | | parts by mass | — | — | — | — | — | — | — |
| | | | | TERATHANE 250 | | parts by mass | — | — | — | — | — | — | — |
| | | | | Selenol 1000 | | parts by mass | — | — | — | — | — | — | — |
| | | | | R[NCO]/[OH] | | | 5.464 | 5.464 | 5.464 | 5.464 | 5.464 | 5.464 | 5.464 |
| | | | Total | | | parts by mass | 85.71 | 85.71 | 85.71 | 85.71 | 85.71 | 85.71 | 85.71 |
| | | TPU | Thermoplastic polyurethane (TPU) type | | | | A | B | C | D | E | F | G |
| | | | Chain extender | 1,4-BD | | parts by mass | 14.3 | 14.3 | 14.3 | 14.3 | 14.3 | 14.3 | 14.3 |
| | | | | 1,3-PDO | | parts by mass | — | — | — | — | — | — | — |
| | | | | 1,6-HDO | | parts by mass | — | — | — | — | — | — | — |
| | | | | CHDM-D | | parts by mass | — | — | — | — | — | — | — |
| | | | Acryl-modified polyorganosiloxane | Chaline R-170S | | parts by mass (relative to TPU) | 0 | 0.007 | 0.03 | 0.06 | 0.15 | 0.6 | 1.2 |
| | Evaluation | | Hardness | | | Shore D | 50 | 50 | 50 | 50 | 50 | 50 | 50 |
| | | | Hard segment concentration | | | mass % | 45 | 45 | 45 | 45 | 45 | 45 | 45 |
| | | | Biobased content | | | % | 50 | 50 | 50 | 50 | 50 | 50 | 50 |
| | | | Specific gravity | | | | 1.10 | 1.10 | 1.10 | 1.10 | 1.10 | 1.10 | 1.10 |
| | | | Strength at break | | | MPa | 45 | 44 | 40 | 43 | 43 | 38 | 36 |
| | | | Elongation at break | | | % | 460 | 470 | 450 | 460 | 460 | 450 | 440 |
| | | | tanδ peak 1 | | | °C. | 45 | 45 | 45 | 45 | 45 | 45 | 45 |
| | | | tanδ peak 2 | | | °C. | −52 | −52 | −52 | −53 | −53 | −53 | −52 |
| Eyewear Frame | Evaluation | | Frame type | | | | A | B | C | D | E | F | G |
| | | | Fit | | | | 5 | 5 | 5 | 5 | 5 | 5 | 3 |
| | | | Surface contact | | | | 3 | 3 | 4 | 5 | 5 | 4 | 4 |
| | | | Bending resistance | | | | 5 | 5 | 5 | 5 | 5 | 5 | 5 |
| | | | Stain resistance | | | Sun oil resistance | 3 | 3 | 4 | 5 | 5 | 5 | 5 |
| | | | Paintwork (Gloss) | | | Coating agent | 89 | 89 | 90 | 89 | 87 | 80 | 40 |
| | | | Paintwork (Adherence) | | | Coating agent | 5B | 5B | 5B | 5B | 5B | 3B | 1B |

TABLE 2

| | | | | | | | Ex. 8 | Ex. 9 | Ex. 10 | Ex. 11 | Ex. 12 |
|---|---|---|---|---|---|---|---|---|---|---|---|
| Eyewear material | Mixing formulation | Prepolymer | | Prepolymer type | | | b | c | d | e | f |
| | | | | Synthesis Ex. | | | 3 | 4 | 5 | 6 | 7 |
| | | | Polyisocyanate component | 1,4-BIC | parts by mass | | 42.6 | 42.5 | 46.4 | 33.8 | 30.8 |
| | | | | 1,3-BIC | parts by mass | | — | — | — | — | — |
| | | | | H12MDI | parts by mass | | — | — | — | — | — |
| | | | Active hydrogen group containing component | PTG2000SN (P) | parts by mass | | 22.0 | 20.6 | 17.5 | 27.7 | 28.3 |
| | | | | PTG1000SN (P) | parts by mass | | 21.3 | 20.1 | 17.1 | 27.7 | 30.1 |
| | | | | PTG650 | parts by mass | | — | — | — | — | — |
| | | | | TERATHANE 250 | parts by mass | | — | — | — | — | — |
| | | | | selenol1000 | parts by mass | | — | — | — | — | — |
| | | | | R[NCO]/[OH] | | | 6.748 | 7.165 | 9.222 | 4.182 | 3.332 |
| | | | | Total | parts by mass | | 85.91 | 83.31 | 81.01 | 89.21 | 89.21 |
| | | TPU | | Thermoplastic polyurethane (TPU) type | | | H | I | J | K | L |
| | | | Chain extender | 1,4-BD | parts by mass | | — | 16.8 | 19.0 | 5.9 | 10.1 |
| | | | | 1,3-PDO | parts by mass | | 14.1 | — | — | — | — |
| | | | | 1,6-HDO | parts by mass | | — | — | — | 7.7 | — |
| | | | | CHDM-D | parts by mass | | — | — | — | — | — |
| | | | Acryl-modified polyorganosiloxane | Chaline R-170S | parts by mass (relative to TPU) | | 0.06 | 0.06 | 0.06 | 0.06 | 0.06 |
| | Evaluation | | | Hardness | shoreD | | 45 | 59 | 72 | 45 | 43 |
| | | | | Hard segment concentration | mass % | | 50 | 53 | 60 | 38 | 32 |
| | | | | Biobased content | % | | 46 | 43 | 37 | 57 | 61 |
| | | | | Specific gravity | | | 1.12 | 1.13 | 1.12 | 1.09 | 1.09 |
| | | | | Strength at break | MPa | | 31 | 41 | 43 | 33 | 31 |
| | | | | Elongation at break | % | | 490 | 390 | 280 | 400 | 450 |
| | | | | tanδ peak 1 | °C. | | 33 | 47 | 59 | 37 | 34 |
| | | | | tanδ peak 2 | °C. | | −46 | −58 | −63 | −53 | −52 |
| Eyewear Frame | Evaluation | | | Frame type | | | H | I | J | K | L |
| | | | | Fit | | | 5 | 4 | 4 | 5 | 5 |
| | | | | Surface contact | | | 5 | 5 | 5 | 5 | 5 |
| | | | | Bending resistance | | | 5 | 5 | 4 | 5 | 5 |
| | | | | Stain resistance | Sun oil resistance | | 5 | 5 | 5 | 5 | 4 |
| | | | | Paintwork (Gloss) | Coating agent | | 89 | 89 | 89 | 89 | 89 |
| | | | | Paintwork (Adherence) | Coating agent | | 5B | 5B | 5B | 5B | 5B |

TABLE 3

| | | | | | | | Ex. 13 | Ex. 14 | Ex. 15 | Ex. 16 | Ex. 17 | Ex. 18 |
|---|---|---|---|---|---|---|---|---|---|---|---|---|
| Eyewear material | Mixing formulation | Prepolymer | | Prepolymer type | | | g | g | h | h | i | j |
| | | | | Synthesis Ex. | | | 8 | 8 | 9 | 9 | 10 | 11 |
| | | | Polyisocyanate component | 1,4-BIC | parts by mass | | 43.8 | 43.8 | 42.9 | 42.0 | 23.2 | 3.0 |
| | | | | 1,3-BIC | parts by mass | | — | — | — | — | 23.2 | — |
| | | | | H12MDI | parts by mass | | — | — | — | — | — | 37.1 |
| | | | Active hydrogen group containing component | PTG2000SN (P) | parts by mass | | — | — | — | — | 17.5 | 23.8 |
| | | | | PTG1000SN (P) | parts by mass | | — | — | — | — | 17.1 | 25.3 |
| | | | | PTG650 | parts by mass | | — | — | — | — | — | — |

TABLE 3-continued

|  |  |  |  |  | No. | | | | | |
|---|---|---|---|---|---|---|---|---|---|---|
|  |  |  |  |  | Ex. 13 | Ex. 14 | Ex. 15 | Ex. 16 | Ex. 17 | Ex. 18 |
|  |  |  | TERATHANE 250 | parts by mass | — | — | — | — | — | — |
|  |  |  | selenol1000 | parts by mass | 42.1 | 42.1 | 42.2 | 42.2 | — | — |
|  |  | R[NCO]/[OH] |  |  | 5.839 | 5.839 | 5.718 | 5.599 | 9.222 | 4.160 |
|  |  |  | Total | parts by mass | 85.91 | 85.91 | 85.11 | 84.21 | 81.01 | 89.21 |
|  | TPU | Thermoplastic polyurethane (TPU) type |  |  | M | N | O | P | Q | R |
|  |  | Chain extender | 1,4-BD | parts by mass | — | — | 6.9 | 15.8 | 19.0 | 10.7 |
|  |  |  | 1,3-PDO | parts by mass | 14.1 | 14.1 | 8.1 | — | — | — |
|  |  |  | 1,6-HDO | parts by mass | — | — | — | — | — | — |
|  |  |  | CHDM-D | parts by mass | — | — | — | — | — | — |
|  | Acryl-modified polyorganosiloxane |  | Chaline R-170S | parts by mass (relative to TPU) | 0 | 0.06 | 0.06 | 0.06 | 0.06 | 0.06 |
|  | Evaluation | Hardness |  | shoreD | 50 | 50 | 56 | 61 | 50 | 45 |
|  |  | Hard segment concentration |  | mass % | 50 | 50 | 50 | 50 | 60 | 41 |
|  |  | Biobased content |  | % | 55 | 55 | 55 | 55 | 37 | 51 |
|  |  | Specific gravity |  |  | 1.14 | 1.14 | 1.13 | 1.12 | 1.10 | 1.10 |
|  |  | Strength at break |  | MPa | 37 | 35 | 38 | 42 | 31 | 35 |
|  |  | Elongation at break |  | % | 440 | 420 | 390 | 350 | 450 | 350 |
|  |  | tanδ peak 1 |  | ° C. | 44 | 44 | 42 | 44 | 31 | 40 |
|  |  | tanδ peak 2 |  | ° C. | −46 | −46 | −47 | −48 | −45 | −49 |
| Eyewear Frame | Evaluation | Frame type |  |  | M | N | O | P | Q | R |
|  |  | Fit |  |  | 5 | 5 | 5 | 5 | 5 | 5 |
|  |  | Surface contact |  |  | 3 | 5 | 5 | 5 | 5 | 5 |
|  |  | Bending resistance |  |  | 5 | 5 | 5 | 5 | 4 | 4 |
|  |  | Stain resistance |  | Sun oil resistance | 3 | 5 | 5 | 5 | 5 | 4 |
|  |  | Paintwork (Gloss) |  | Coating agent | 90 | 89 | 89 | 89 | 88 | 89 |
|  |  | Paintwork (Adherence) |  | Coating agent | 5B | 5B | 5B | 5B | 5B | 5B |

TABLE 4

|  |  |  |  |  |  | No. | | |
|---|---|---|---|---|---|---|---|---|
|  |  |  |  |  |  | Comp. Ex. 1 | Comp. Ex. 2 | Comp. Ex. 3 |
| Eyewear material | Mixing formulation | Prepolymer |  | Prepolymer type |  | k | l | One shot method |
|  |  |  |  | Synthesis Ex. |  | 12 | 13 | — |
|  |  |  | Polyisocyanate component | 1,4-BIC | parts by mass | 28.4 | 28.3 | 26.5 |
|  |  |  |  | 1,3-BIC | parts by mass | 28.4 | — | 29.4 |
|  |  |  |  | H12MDI | parts by mass | — | — | — |
|  |  |  | Active hydrogen group containing component | PTG2000SN (P) | parts by mass | — | — | — |
|  |  |  |  | PTG1000SN (P) | parts by mass | — | — | — |
|  |  |  |  | PTG650 | parts by mass | — | — | 5.9 |
|  |  |  |  | TERATHANE 250 | parts by mass | 3.5 | — | — |
|  |  |  |  | selenol1000 | parts by mass | — | 65.2 | — |
|  |  | R[NCO]/[OH] |  |  |  | 20.892 | 2.437 | — |
|  |  |  |  | Total | parts by mass | 60.31 | 93.51 | 61.87 |
|  | TPU | Thermoplastic polyurethane (TPU) type |  |  |  | S | T | U |
|  |  | Chain extender | 1,4-BD |  | parts by mass | — | — | — |
|  |  |  | 1,3-PDO |  | parts by mass | — | 6.5 | — |

TABLE 4-continued

|  |  |  |  | Comp. Ex. 1 | Comp. Ex. 2 | Comp. Ex. 3 |
|---|---|---|---|---|---|---|
|  |  | 1,6-HDO | parts by mass | — | — | 13.5 |
|  |  | CHDM-D | parts by mass | 39.7 | — | 24.7 |
|  | Actyl-modified polyorganosiloxane | Chaline R-170S | parts by mass (relative to TPU) | 0.06 | 0.06 | 0.06 |
| Evaluation | Hardness |  | shoreD | 80 | 35 | 80 |
|  | Hard segment concentration |  | mass % | 93 | 23 | 93 |
|  | Biobased content |  | % | 0 | 70 | 0 |
|  | Specific gravity |  |  | 1.10 | 1.08 | 1.10 |
|  | Strength at break |  | MPa | 70 | 23 | 69 |
|  | Elongation at break |  | % | 20 | 600 | 18 |
|  | tanδ peak 1 |  | ° C. | 112 | none | 85 |
|  | tanδ peak 2 |  | ° C. | −55 | −48 | None |
| Eyewear Frame Evaluation | Frame type |  |  | S | T | U |
|  | Fit |  |  | 2 | 2 (soft) | 2 |
|  | Surface contact |  |  | 3 | 3 | 3 |
|  | Bending resistance |  |  | 3 | 3 | 3 |
|  | Stain resistance |  | Sun oil resistance | 5 | 4 | 5 |
|  | Paintwork (Gloss) |  | Coating agent | 90 | 90 | 88 |
|  | Paintwork (Adherence) |  | Coating agent | 5B | 5B | 5B |

The abbreviations in Tables are described in detail below.
1,4-BIC: 1,4-bis(isocyanatomethyl) cyclohexane produced in Synthesis Example 1
1,3-BIC: 1,3-bis(isocyanatomethyl) cyclohexane, trade name: TAKENATE 600 (Manufactured by Mitsui Chemicals)
H12MDI: $H_{12}$MDI, methylenebis(cyclohexyl isocyanate)
PTG2000SN (P): number average molecular weight 2000, polytetramethylene ether glycol in which biomass material is used (Manufactured by Hodogaya Chemical Co., LTD.)
PTG1000SN (P): number average molecular weight 1000, polytetramethylene ether glycol in which biomass material is used (Manufactured by Hodogaya Chemical Co., LTD.)
PTG650SN: number average molecular weight 650, polytetramethylene ether glycol composed of tetrahydrofuran (Manufactured by Hodogaya Chemical Co., LTD.)
TERATHANE 250: number average molecular weight 250, polytetramethylene ether glycol composed of tetrahydrofuran (manufactured by INVISTA)
Selenol H1000: polytrimethyleneetherglycol in which biomass material is used (manufactured by Du Pont Kabushiki Kaisha)
1,4-BD: 1,4-butanediol (Manufactured by Wako Pure Chemical Industries, Ltd.)
1,3-PDO: 1,3-propanediol (Manufactured by Wako Pure Chemical Industries, Ltd.)
1,6-HDO: 1,6-hexanediol (Manufactured by Wako Pure Chemical Industries, Ltd.)
1,4-CHDM: 1,4-cyclohexanedimethanol (Manufactured by Wako Pure Chemical Industries, Ltd.)
Chaline R-170S: manufactured by Nissin Chemical Industry Co., Ltd. acryl-modified polyorganosiloxane While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY

The eyewear material, eyewear frame, and eyewear of the present invention are suitably used in various eyewear industries of corrective glasses, protection glasses, sunglasses, and goggles.

The invention claimed is:

1. An eyewear material which is
a preparation prepared from thermoplastic polyurethane as a reaction product produced by reaction of a polyisocyanate component containing methylenebis(cyclohexyl isocyanate) and/or bis(isocyanatomethyl) cyclohexane with an active hydrogen group-containing component, and
used in production of at least one kind selected from the group consisting of an eyewear frame, a nose pad, an earpiece, a temple, a rim, a bridge, an end piece and a hinge,
wherein the eyewear material has a tan δ peak at both less than 0° C. and 0° C. or more and 70° C. or less observed in dynamic viscoelasticity measurement in tensile mode under the measurement conditions of a temperature increase speed of 5° C./min and a measurement frequency of 10 Hz.

2. The eyewear material according to claim 1, wherein
the thermoplastic polyurethane is obtained by a prepolymer method of first allowing the polyisocyanate component to react with a portion of the active hydrogen group-containing component, and then, allowing the obtained isocyanate group-terminated prepolymer to react with a chain extender which is the remaining portion of the active hydrogen group-containing component, and
the thermoplastic polyurethane has a hard segment concentration of 25 mass % or more and 70 mass % or less calculated by the following formula:

[chain extender (g)+(chain extender (g)/molecular weight of chain extender (g/mol))×average molecular weight of polyisocyanate component (g/mol)]÷(polyisocyanate component (g)+active hydrogen group-containing component (g))× 100.

3. The eyewear material according to claim 1, wherein the thermoplastic polyurethane is a reaction product produced by reaction of the polyisocyanate component containing bis(isocyanatomethyl) cyclohexane with the active hydrogen group-containing component.

4. The eyewear material according to claim 1, further comprising 0.01 parts by mass or more and 1 part by mass or less of acryl-modified organopolysiloxane relative to 100 parts by mass of the thermoplastic polyurethane.

5. An eyewear frame formed from an eyewear material which is
a preparation prepared from thermoplastic polyurethane as a reaction product produced by reaction of a polyisocyanate component containing methylenebis(cyclohexyl isocyanate) and/or bis(isocyanatomethyl) cyclohexane with an active hydrogen group-containing component, and
used in production of at least one kind selected from the group consisting of an eyewear frame, a nose pad, an earpiece, a temple, a rim, a bridge, an end piece and a hinge,
wherein the eyewear material has a tan δ peak at both less than 0° C. and 0° C. or more and 70° C. or less observed in dynamic viscoelasticity measurement in tensile mode under the measurement conditions of a temperature increase speed of 5° C./min and a measurement frequency of 10 Hz.

6. The eyewear frame according to claim 5, wherein the eyewear frame is coated with a polyurethane coating agent containing aliphatic polyisocyanate.

7. The eyewear frame according to claim 6, wherein the aliphatic polyisocyanate contains pentamethylenediisocyanate and/or a derivative thereof.

8. An eyewear comprising:
an eyewear frame and an optical lens attached to the eyewear frame,
wherein the eyewear frame is formed from an eyewear material, which is
a preparation prepared from thermoplastic polyurethane as a reaction product produced by reaction of a polyisocyanate component containing methylenebis(cyclohexyl isocyanate) and/or bis(isocyanatomethyl) cyclohexane with an active hydrogen group-containing component, and
used in production of at least one kind selected from the group consisting of an eyewear frame, a nose pad, an earpiece, a temple, a rim, a bridge, an end piece and a hinge, and
the eyewear material has a tan δ peak at both less than 0° C. and 0° C. or more and 70° C. or less observed in dynamic viscoelasticity measurement in tensile mode under the measurement conditions of a temperature increase speed of 5° C./min and a measurement frequency of 10 Hz.

9. The eyewear according to claim 8, wherein the optical lens is formed from a biomass material.

* * * * *